United States Patent
Lieber et al.

(12)

(10) Patent No.: US 6,686,196 B2
(45) Date of Patent: Feb. 3, 2004

(54) RECOMBINANT, MODIFIED ADENOVIRAL VECTORS FOR TUMOR SPECIFIC GENE EXPRESSION AND USES THEREOF

(75) Inventors: André Lieber, Seattle, WA (US); Dirk S. Steinwaerder, Hamburg (DE); Cheryl A. Carlson, Seattle, WA (US); Jie Mi, Seattle, WA (US)

(73) Assignee: University of Washington, Seattle, WA (US)

( * ) Notice: Subject to any disclaimer, the term of this patent is extended or adjusted under 35 U.S.C. 154(b) by 209 days.

(21) Appl. No.: 09/849,106

(22) Filed: May 3, 2001

(65) Prior Publication Data

US 2002/0037280 A1 Mar. 28, 2002

Related U.S. Application Data

(60) Provisional application No. 60/202,367, filed on May 3, 2000.

(51) Int. Cl.[7] .............................................. C12N 15/861

(52) U.S. Cl. .................... 435/320.1; 435/455; 435/456; 424/93.2

(58) Field of Search ...................... 424/93.2; 435/320.1, 435/69.1, 455, 456, 463, 465, 91.4

(56) References Cited

U.S. PATENT DOCUMENTS

5,871,982 A * 2/1999 Wilson et al. ............... 435/457

OTHER PUBLICATIONS

Grable et al. "cis and trans requirements for the selective packaging of adenovirus type 5 DNA," J. Virol. 66 (2): 723–731, Feb. 1992.*
Lieber et al. "Intgegrating adenovirus–adeno–associated virus hybrid vectors devoid of all viral genes," J. Virol. 73 (11): 9314–9324, Nov. 1999.*
Kirn, D. H., and F. McCormick. 1996. *Mol Med Today.* 2:519–527.
Vousden, K. H. 1995 "Regulation of the cell cycle by viral onocoproteins," *Semin Cancer Biol.* 6:109–116.
Algate PA, et al., Regulation of the interleukin–3 (IL–3) receptor by IL–3 in the fetal liver–derived FL5.12 cell line. *Blood,* 1994, May 1, 83(9):2459–2468.
Babiss, L. E. and H. S. Ginsberg. 1984.*J. Virol.* 50:202–212.
Babiss, L.E., et al. 1986 *Mol Cell Biol* 6, 3798–3806.
Berk, A. J. et al., 1979, *Cell.* 17:935–944.
Bett, A.J., et al. 1994, *Proc Natl Acad Sci U S A* 91:8802–8806.
Bischoff, J. R. et al., 1996. *Science.* 274:373–376.
Bjorklund, S. et al., 1990. *Biochemistry.* 29:5452–5458.
Breviario F, et al., Interleukin–1–inducible genes in endothelial cells. Cloning of a new gene related to C–reactive protein and serum amyloid P component. *Journal of Biological Chemistry,* 1992, Nov 5, 267(31):22190–22197.
Cluitmans FH, et al., IL–4 down–regulated IL–2–, IL–3–, and GM–CSF–induced cytokine gene expression in peripheral blood monocytes. Annals of Hematology, (1994) Jun., 68(6):293–298.
Barkats et al. 1998 *Prog Neurobiol* Jul.;55(4):333–341.
Curiel, DT., 1999 *Ann N Y Acad Sci* 886:158–171.
Dachs, G.U., et al. (1997) *Oncol Res* 9, 313–325.
Danthinne, X. and Imperiale MJ 2000 *Gene Ther* Oct.;7(20):1707–1714.
de Wit H, et al., Differential regulation of M–CSF and IL–6 gene expression in monocytic cells. *British Journal of Haematology,* 1994 Feb., 86(2):259–264.
Debbas, M. and E. White. 1993. *Genes Dev.* 7:546–554.
Dyson, N., 1998. *Genes Dev.* 12:2245–2262.
el–Deiry, W. S. et al., 993. *Cell.* 75:817–25.
Engelhardt, J. F. et al., 1993. *Hum Gene Ther.* 4:759–769.
Englehardt, J. F. et al., 1994. *Hum Gene Ther.* 5:1217–1229.
Engstrom, Y. et al., 1985. *J. Biol Chem.* 260:9114–9116.
Espinoza–Delgado I, et al., Regulation of IL–2 receptor subunit genes in human monocytes. Differential effects of IL–2 and IFN–gamma. *Journal of Immunology,* 1992, Nov. 1, 149(9):2961–2968.
Feldman, LJ, et al. 1996 *Semin Inter Cardiol* Sep.;1(3):202–208.
Gaynor, R. B., and A. J. Berk. 1983. *Cell.* 33:683–693.
Gjorup. O.V., et al. 1994, *Proc Natl Acad Sci U S A* 91:12125–12129.
Goodrum, F. D., and D. A. Ornelles. 1998. *J Virol.* 72:9479–9490.
Halbert, C.L., et al. 1991 *J Virol* 65:473–478.
Hall, A. R. et al., 1998. *Nat Med.* 4:1068–1072.
Hanahan, D. & Weinberg, R.A. 2000 *Cell* 100:57–70.
Harada, J. N., and A. J. Berk. 1999. *J. Virol.* 73:5333–5344.
Hasty et al. (1991) *Molec. Cell. Biol.* 11: 5586–5591.
Hay, J. G. et al., 1999. *Hum Gene Ther.* 10:579–590.
Heise, C. C. et al., 1999. *Cancer Res.* 59:2623–2628.
Heise, C. et al., 1997. *Nat Med.* 3:639–645.
Hiebert, S. W. et al., 1989, *Proc Natl Acad Sci U S A.* 86:3594–8.
Hitt, M. M. et al., 1997. *Advances in Pharmacology.* 40:137–205.

(List continued on next page.)

*Primary Examiner*—Scott D. Priebe
(74) *Attorney, Agent, or Firm*—Mandel & Adriano

(57) ABSTRACT

This invention provides modified recombinant Ad vectors (e.g., AdE1– vectors) undergoing defined homologous recombination in order to create predictably rearranged genomic derivatives in a host cell. Genomic rearrangements can be achieved, for example, by incorporating two IR sequences within one vector genome and enabling genomic rearrangement by coinfection with two parental vectors of one type (also referred to herein as a one vector system) or by homologous recombination of overlapping regions in two distinct types of parental vectors (with or without IR sequences) and enabling genomic rearrangement only upon coinfection of the host cell with the two distinct parental vectors (also referred to herein as two vector system).

26 Claims, 27 Drawing Sheets

OTHER PUBLICATIONS

Horisberger MA, et al., Cloning and sequence analyses of cDNAs for interferon– and virus–induced human Mx proteins reveal that they contain putative guanine nucleotide–binding sites: functional study of the corresponding gene promote. *Journal of Virology,* 1990 Mar., 64(3):1171–1181.
Jane, S. M. et al., 1998. *Ann. Med.* 30:413–415.
Jones, N., and T. Shenk. 1979. *Proc Natl Acad Sci U S A.* 76:3655–3669.
Kamb, A. et al., 1994. *Science.* 264:436–440.
Kao, C. Y. et al., 1999. *J. Biol Chem.* 274:23043–51.
Kay AB, et al., Messenger RNA expression of the cytokine gene cluster, interleukin 3 (IL–3), IL–4, IL–5, and granulocyte/macrophage colony–stimulating factor, in allergen–induced late–phase cutaneous reactions in atopic subjects. *Journal of Experimental Medicine,* 1991 Mar. 1, 173(3):775–778.
Kay, M.A. et al. *Hepatology* (1995) 21: 815–819.
Kovesdi, I., et al. 1997 *Curr Opin Biotechnol* Oct.;8(5):583–589.
Lagoo, AS, et al., IL–2–IL–4, and IFN–gamma gene expression versus secretion in superantigen–activated T cells. Distinct requirement for costimulatory signals through adhesion molecules. *Journal of Immunology,* 1994 Feb. 15, 152(4):1641–1652.
Lee, M.G., et al. 1995 *Mol Cell Boil Hum Dis Ser* 5:20–32.
Li YP et al., Proinflammatory cytokines tumor necrosis factor–alpha and IL–6, but not IL–1, down–regulate the osteocalcin gene promoter. *Journal of Immunology,* 1992 Feb. 1, 148(3):788–794.
Lieber, A. et al. 1997 *J Virol* 71, 8798–8807.
Lieber, A., et al. 1996 *J Virol* 70, 8944–8960.
Lowe, S. W. et al., 1994. *Science.* 266:807–810.
Lukashok, SA, et al. 1998 *Curr Clin Top Infect Dis* 18:286–305.
Lum, L. S. et al., 1992. *Mol Cell Biol.* 12:2599–605.
Martinez OM, et al., IL–2 and IL–5 gene expression in response to alloantigen in liver allograft recipients and in vitro. *Transplantation,* 1993 May, 55(5):1159–1166.
Mauviel A, et al., Leukoregulin, a T cell–derived cytokine, induces IL–8 gene expression and secretion in human skin fibroblasts. Demonstration and secretion in human skin fibroblasts. Demonstration of enhanced NK–κβ Binding and NK–κβ–driven promoter activity. *Journal of Immunology,* Nov. 1, 1992 149(9):2969–2976.
Miyashita, T., and J. C. Reed. 1995. *Cell.* 80:293–299.
Nelson, J. E., and M. A. Kay. 1997. *J Virol.* 71:8902–8907.
Nevins, J. R. 1981. *Cell.* 26:213–220.
Okamoto, A. et al., 1994. *Proc Natl Acad Sci U S A.* 91:11045–11049.
Ornelles, D. A., and T. Shenk. 1991. *J Virol.* 65:424–439.
Pang G, et al., GM–CSF, IL–1 alpha, IL–1 β, IL–6, IL–8, IL–10, ICAM–1 and VCAM–1 gene expression and cytokine production in human duodenal fibroblast stimulated with lipopolysaccharide, IL–1 alpha and TNF–alpha. *Clinical and Experimental Immunology,* 1994 Jun., 96(3):437–443.
Parr, M.J. et al. 1997 *Nat Med* 3, 1145–1149.
Pizarro TT, et al. Induction of TNF alpha and TNF β gene expression in rat cardiac transplants during allograft rejection. *Transplantation,* Aug. 1993, 56(2):399–404.

Rao, L. et al., 1992. *Proc Natl Acad Sci U S A.* 89:7742–7746.
Ring, C.J., et al., 1996 *Gene Ther* 3, 1094–103.
Robbins, PD., et al. 1998 *Trends Biotechnol* Jan.; 16(1):35–40.
Rothmann, T. et al., 1998. *J Virol.* 72:9470–9478.
Rubnitz and Subramani (*Mol. and Cell. Biol.* 4:2253–2258, (1984).
Schaack, J., et al. 1996 *Virology* 216, 425–430.
Shi, Q., et al. 1997 *Hum Gene Ther* Mar. 1;8(4):403–410.
Shimane M, et al., Molecular cloning and characterization of G–CSF induced gene cDNA. *Biochemical and Biophysical Research Communications,* 1994 Feb. 28, 199(1):26–32.
Shulman et al. (1990) *Molec. Cell. Biol.* 10:4466–4472.
Smith, GM., et al. 1998 *Arch Neurol* Aug.;(8):1061–1064.
Spitkovsky, D. et al., 1995. *Oncogene.* 10:2421–2425.
Sprecher E, et al., Detection of IL–1 β, TNF–α, and IL–6 gene transcription by the polymerase chain reaction in keratinocytes, Langerhans cells and peritoneal exudate cells during infection with herpes simplex virus–1. *Archives of Virology,* 1992, 126(1–4):253–269.
Steinwaerder, D, et. Al., 2001 *Nature Medicine* 7:2; 240–243.
Steinwaerder, D.S. and A. Lieber, 2000, *Gene Therapy* 7:556–567.
Steinwaerder, et al. 1999, *J Virol* 73, 9303–9313.
Stratford–Perricaudet, L.D., et al. 1992 *J Clin Invest* 90, 626–630.
Sussenbach, J.S. & van der Vliet, 1973 *P.C. Virology* 54, 299–303.
Teodoro, J. G. et al., 1995. *Oncogene.* 11:467–474.
Tevethia, M.J. & Spector, D.J. 1984 *Virology* 137, 428–431.
Tevethia, M.J. & Spector, D.J. 1989 *Prog Med Virol* 36, 120–190.
Tiainen, M. et al., 1996. *Cell Growth Differ.* 7:1039–1050.
Turnell, A. S. et al., 1999. *J Virol.* 73:2074–2083.
Ulich TR, et al., Endotoxin–induced cytokine gene expression in vivo. III. IL–6 mRNA and serum protein expression and the in vivo hematologic effects of IL–6. *Journal of Immunology,* 1991 Apr. 1, 146(7):2316–2323.
Vollmer, C. M. et al., 1999. *Cancer Res.* 59:4369–4374.
Vrancken Peeters, et al. 1996 *BioTechniques* 20, 278–285.
Vrancken Peeters, M.J., et al. 1997 *Hepatology* 25:884–888.
Wildner, O. et al. 1999 *Gene Ther* 6:57–62.
Wildner, O. et al, 1999. *Cancer Res.* 59:410–413.
Wong G, et al., Human GM–CSF: Molecular cloning of the complementary DNA and purification of the natural and recombinant proteins. *Science* 1985, 228:810–815.
Xiong, Y. et al., 1993. *Nature.* 366:701–704.
Xu, Z.Z., et al. 1997 *Viriology* Mar. 31;230(1):62–71.
Yang, Y. et al., 1994. *Proc Natl Acad Sci U S A.* 91:4407–4411.
Yang, Y. et al., 1996. *J Virol.* 70:7209–7212.
Zhang, W.W. 1999 *Cancer Gene Ther* 6, 113–138.
Zhang, W.W., et al. 1995 *Biotechniques* 18, 444–447.
Zhang, W.W., et al. 1999 *Thromb Haemost* Aug.;82(2):562–571.
Di Donato, J., et al, *Mol.Cell.Biol.* 16: 1295–1304, 1996.

* cited by examiner

FIG. 4
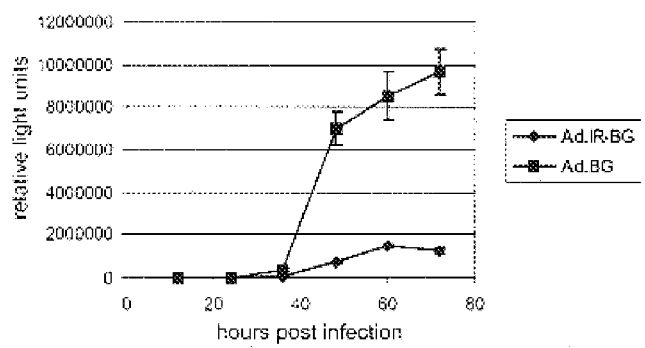
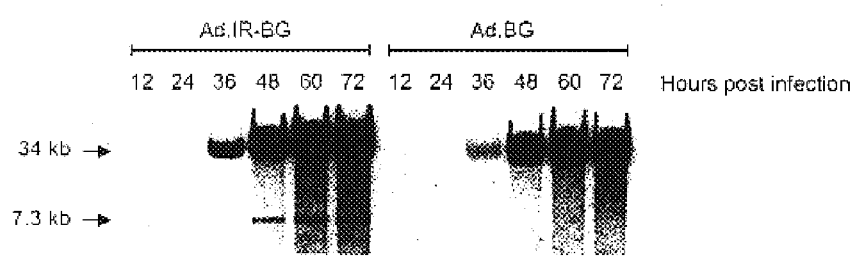
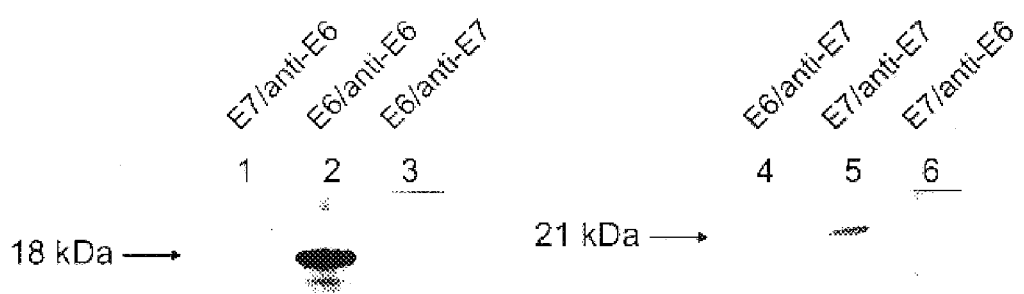
FIG. 5A

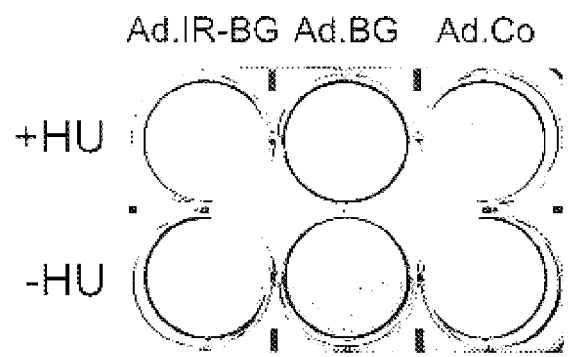
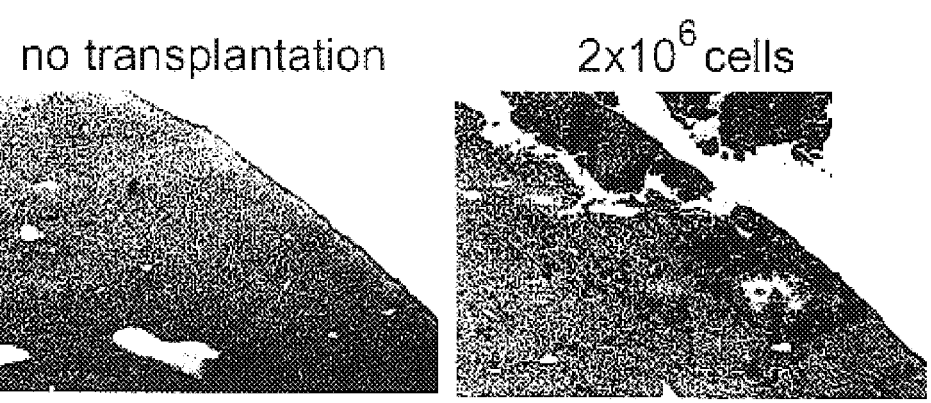
FIG. 10

FIG. 17

VIRAL DNA REPLICATION RATIOS IN CORRELATION WITH DEVELOPMENT OF CPE AND p53, pRb, AND p16 STATUS OF TUMOR CELLS.

| CELL LINE | REPLICATION RATIO[1] | CPE[2] | p53[3] | pRb[3] | p16[3] |
|---|---|---|---|---|---|
| HepG2 | +++ | ++ | +(wt) | + | + |
| MCF-7 | +++ | +/- | +(wt) | + | - |
| LS 174 T | + | - | +(wt) | + | - |
| HUH7 | +++ | - | +(mut) | + | - |
| LOVO | +++++ | +++ | - | + | - |
| BT-549 | + | - | - | - | + |
| Hep3B | ++ | - | +(mut) | - | + |
| HeLa | +++++ | + | +[3] | +[3] | ? |
| 293 | ++++++ | +++ | +[3] | +[3] | ? |

THE SOUTHERN BLOT ANALYSIS SHOWN IN FIG. 3 WAS QUANTIFIED BY PHOSPHO-IMAGING AND THE RATIO OF REPLICATED TO NON-REPLICATED VIRAL DNA WAS DETERMINED AFTER CORRECTION FOR INCOMPLETE METHYLATION (SEE MATERIAL AND METHODS).
[1] REPLICATION RATIO AT THE HIGHEST VIRUS CONCENTRATION EMPLOYED.
+=1-5, ++=6-10, +++=11-15, ++++=16-20, +++++=20-50, ++++++=>50
[2] GRADE OF DEVELOPMENT OF VISUAL CYTOPATHIC EFFECT 72H AFTER INFECTION AT THE HIGHEST VIRUS CONCENTRATION EMPLOYED. (+=NO CPE, +++=STRONG CPE)
[3] SEE TABLE 1

FIG. 20B

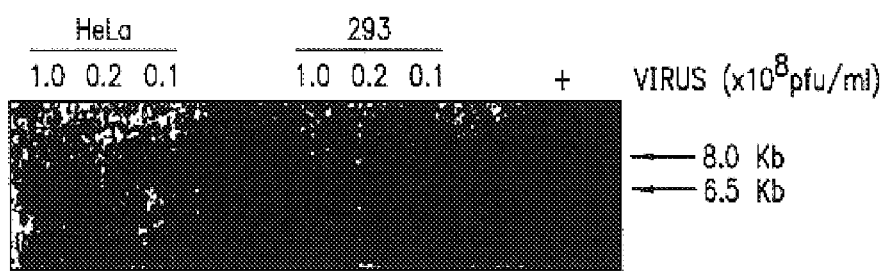

FIG. 19A
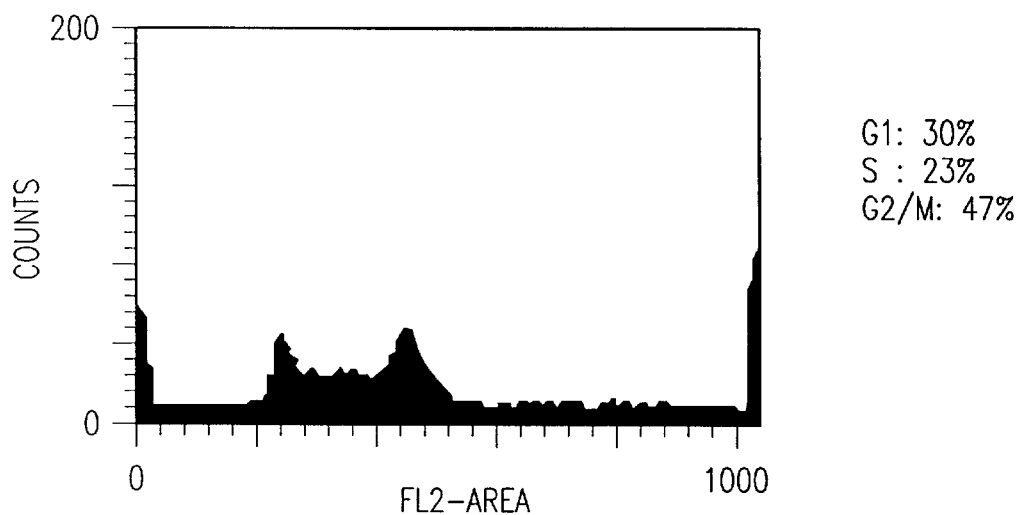
G1: 30%
S : 23%
G2/M: 47%
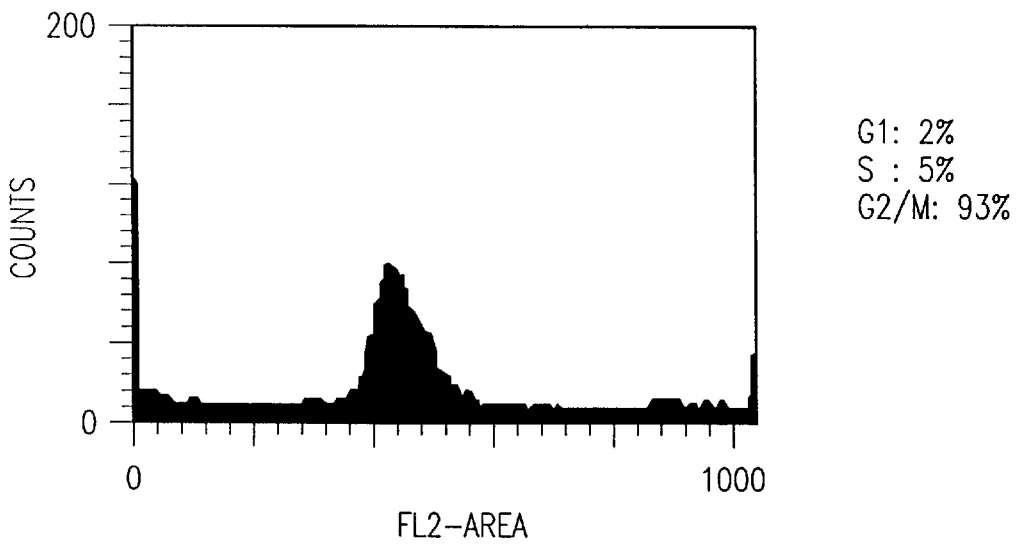
G1: 2%
S : 5%
G2/M: 93%

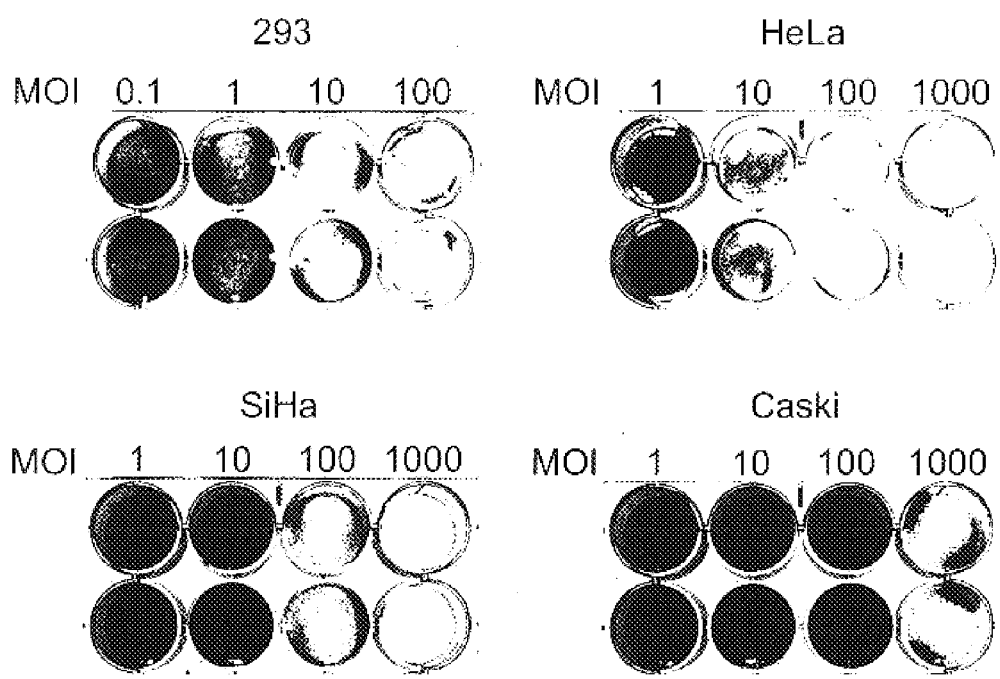

RECOMBINANT, MODIFIED ADENOVIRAL VECTORS FOR TUMOR SPECIFIC GENE EXPRESSION AND USES THEREOF

This application is based on a provisional application, U.S. Serial No. 60/202,367, filed May 3, 2000, the contents of which are hereby incorporated by reference in their entirety into this application.

This work was supported by NIH grants R21 DK55590 and R01 CA80192 and the Government has certain rights in this invention.

Throughout this application, various publications are referenced. The disclosures of these publications in their entireties, are hereby incorporated by reference into this application, in order to more fully describe the state of the art, as known to those skilled therein, as of the date of invention, described and claimed herein.

FIELD OF THE INVENTION

This invention relates to modified recombinant adenovirus (Ad) vectors which lack a gene or genes for replication of the adenovirus in a non-actively cycling cell but remain capable of specifically replicating in an actively cycling cells. These modified recombinant vectors are useful for regulating transgene expression in cells such as tumor cells and therefore, for treatment of a variety of cancers.

BACKGROUND OF THE INVENTION

Adenovirus Replication

Numerous studies in cell-free systems and in infected cells have established that Ad DNA replication takes place in two steps.

In the first step, DNA synthesis is initiated by the precursor to the terminal protein (pTP). pTP binds as a heterodimer with the Ad polymerase (Pol) to specific sites within the inverted terminal repeat (ITR) sequences. Ad DNA replication begins at both ends of the linear genome resulting in a daughter strand that is synthesized in the 5' to 3' direction displacing the parental strand with the same polarity.

Three non-exclusive mechanisms are proposed for the second stage, the replication of the displaced parental strand: i) displaced single strands can form partial duplexes by base pairing of the ITRs on which a second round of DNA synthesis may be initiated, ii) when two oppositely moving displacement forks meet, the two parental strands will no longer be held together and will separate, resulting in partially duplex and partially single-stranded (ss) molecules; synthesis is then completed on the displaced parental strands, and iii) displaced strands with opposite polarity resulting from initiation at two different molecular ends, can renature to form a double-stranded daughter molecule. Replication of DNA requires two components: DBP and polymerase. DBP is thought to stabilize the formation of the panhandle structure and the interstrand renaturation process. Polymerase synthesizes Ad DNA at a rate of 20–30 base pairs (bp) per second.

Ad DNA replication is a crucial prerequisite in Ad recombination. Suppressing Ad DNA replication diminishes Ad recombination.

Adenovirus Recombination

Ad DNA replication generates large amounts of stabilized ssDNA that has been shown to efficiently induce homologous recombination in bacteria. Electron microscopy (EM) studies demonstrated that the displaced parental single strand can be transferred to another duplex genome forming Holliday structures very similar to the structure described for homologous recombination in bacteria.

Early studies focused on Ad recombination revealed that Ad genomes can recombine until late in the infection cycle and each viral genome can undergo multiple recombination events. Population genetics of Ad genomes suggested a model similar to that proposed for T-even phages. More sophisticated studies analyzing cross-exchange of specific restriction sites demonstrated that recombination between Ad genomes can be detected only after the onset of viral DNA replication and that the degree of replication is proportional to the recombination frequency. Suppressing viral DNA replication unambiguously diminishes recombination.

Recombinant Ad vectors are widely used for gene transfer in vitro and in vivo (Hitt, M. M. et al., 1997. *Advances in Pharmacology.* 40:137–205). First-generation AdE1− vectors used for gene transfer deleted the E1A/E1B genes and are, therefore, considered replication deficient in normal cells (Jones, N., and T. Shenk. 1979. *Proc Natl Acad Sci U S A.* 76:3665–9).

The proteins encoded within the early region 1A (E1A-12S and E1A-13S) and 1B (E1B-55k and -19k) mediate viral replication by transactivating viral gene expression and deregulating the cell cycle [for review: (Shenk, T. 1996. *Adenoviridea,* p. 2111–2148. In B. N. Fields, Knipe, D. M., Howley, P. M. (ed.), *Fields Virology,* vol. 2. Lippincott-Raven Publisher, Philadelphia)]. E1A-12S and 13S are the first proteins expressed from the incoming viral genome and function as the main transactivators for other Ad transcription units, particularly the E2 and E4 regions that encode proteins for Ad DNA replication. E1A deregulates the cell cycle and induces cellular DNA synthesis by directly transactivating cellular genes [(e.g. c-myc (Hiebert, S. W. et al., 1989. *Proc Natl Acad Sci U S A.* 86:3594–8), cdc2 (Kao, C. Y. et al., 1999. *J Biol Chem.* 274:23043–51), hsp70 (Lum, L. S. et al., 1992. *Mol Cell Biol.* 12:2599–605)], as well as by interacting with cell cycle regulatory proteins like pRb, pRb-related proteins (p107/p130), or p300 (Tiainen, M. et al., 1996. *Cell Growth Differ.* 7:1039–50). Binding of E1A to pRb-family members releases transcription factors of the E2F family resulting in transcriptional upregulation of host genes; these genes are regulators or effectors of DNA synthesis [e.g. c-myc, Elf-1, myoD, DNA polymerase a, cyclins A and E, PCNA (Dyson, N., 1998. *Genes Dev.* 12:2245–62)] which eventually drive quiescent cells into S-phase.

These and other cellular factors, whose activities peak during S-phase [e.g. the synthesis of deoxyribonucleotides (Bjorklund, S. et al., 1990. *Biochemistry.* 29:5452–8; Engstrom, Y. et al., 1985. *J Biol Chem.* 260:9114–6)], create an environment appropriate for viral DNA synthesis. However, in normal cells, E1A induced cell cycle deregulation results in the accumulation of p53, which stimulates p53 mediated G1 arrest (el-Deiry, W. S. et al., 993. *Cell.* 75:817–25; Xiong, Y. et al., 1993. *Nature.* 366:701–4) or apoptotic pathways (Miyashita, T., and J. C. Reed. 1995. *Cell.* 80:293–9). Notably, E1A induced apoptosis can also occur through p53 independent pathways (Teodoro, J. G. et al., 1995. *Oncogene.* 11:467–74).

Among the E1B proteins, the 19 kDa and 55 kDa proteins have been shown to cooperate with the E1A-13S product to initiate viral replication by down regulating p53 driven expression of cyclin D1; this is required for cells to progress through the G1 phase of the cell cycle (Spitkovsky, D. et al., 1995. *Oncogene.* 10:2421–5). Another important function of the E1B proteins is to oppose p53-mediated apoptosis induced by E1A-12S. The E1B 55k protein in concert with E4-orf6 and E4-orf3 directly blocks p53, whereas E1B-19k appears to inhibit a p53-dependent, apoptotic downstream event similar to bcl-2 (Debbas, M. and E. White. 1993. *Genes Dev.* 7:546–54; Rao, L. et al., 1992. *Proc Natl Acad Sci U S A.* 89:7742–6). At late time points during lytic infection, E1B complexes to the E4orf6 protein, thereby enhancing the export of viral mRNA from the nucleus while, at the same time, inhibiting the transport of cellular mRNA (Babiss, L. E. and H. S. Ginsberg. 1984. *J Virol.* 50:202–12; Ornelles, D. A., and T. Shenk. 1991. *J Virol.* 65:424–9). E1B-55k inactivation of p53 has been hypothesized to be required for productive (wild type) adenovirus replication resulting in lytic infection (Bischoff, J. R. et al., 1996. *Science.* 274:373–6). Consequently, it has been suggested that an E1B-55k mutant virus should replicate preferentially in p53 deficient tumor cells (Heise, C. et al., 1997. *Nat Med.* 3:639–45; Heise, C. C. et al., 1999. *Cancer Res.* 59:2623–8; Kirn, D. H., and F. McCormick. 1996. *Mol Med Today.* 2:519–27; Wildner, O. et al., 1999. *Cancer Res.* 59:410–3). However, a number of reports have discredited this idea by demonstrating that the ability of the E1B-55k mutant to productively replicate does not correlate with cellular p53 status (Goodrum, F. D., and D. A. Ornelles. 1998. *J Virol.* 72:9479–90; Hall, A. R. et al., 1998. *Nat Med.* 4:1068–72; Harada, J. N., and A. J. Berk. 1999. *J Virol.* 73:5333–44; Hay, J. G. et al., 1999. *Hum Gene Ther.* 10:579–90; Rothmann, T. et al., 1998. *J Virol.* 72:9470–8; Turnell, A. S. et al., 1999. *J Virol.* 73:2074–83; Vollmer, C. M. et al., 1999. *Cancer Res.* 59:4369–74).

Loss of p53 function is coincident with the development of a variety of tumors mostly due to accumulation of mutations and the inability to carry out p53 dependent apoptosis (Lowe, S. W. et al., 1994. *Science.* 266:807–10). Another common defect observed in many different tumors is the loss of control of the G1 to S transition in the cell cycle due to mutation or inactivation of pRb or p16, a kinase inhibitor which regulates the phosphorylation and activity of pRb (Kamb, A. et al., 1994. *Science.* 264:436–40; Okamoto, A. et al., 1994. *Proc Natl Acad Sci U S A.* 91:11045–9; Vousden, K. H. 1995. *Semin Cancer Biol.* 6:109–16). Since AdE1A/E1B inactivate p53 and pRb functions, tumor cell lines with deregulated cell cycles and deregulated p53 and/or pRb pathways may support viral replication in the absence of E1A and E1B.

First generation, E1A/E1B-deleted adenoviruses are used for gene therapy based on the premise that deleting of E1A and E1B sequences should be sufficient to eliminate viral gene expression and replication (Berk, A. J. et al., 1979. *Cell.* 17:935–44; Hitt, M. M. et al., 1997. *Advances in Pharmacology.* 40:137–205; Jones, N., and T. Shenk. 1979. *Proc Natl Acad Sci U S A.* 76:3665–9). However, a large number of studies have demonstrated the expression of viral early and late proteins in cells transduced with E1 deleted AdE1 vectors in vitro and in vivo (Engelhardt, J. F. et al., 1994. *Hum Gene Ther.* 5:1217–29; Engelhardt, J. F. et al., 1993. *Hum Gene Ther.* 4:759–69; Jane, S. M. et al., 1998. *Ann Med.* 30:413–5; Lieber, A. et al., 1996. *J Virol* 70:8944–60; Yang, Y. et al., 1994. *Proc Natl Acad Sci U S A.* 91:4407–11; Yang, Y. et al., 1996. *J Virol.* 70:7209–12). These findings are in agreement with observations made two decades ago that transcription of early Ad genes occurs slowly in the absence of E1A in a dose dependent manner (Gaynor, R. B., and A. J. Berk. 1983. *Cell.* 33:683–93; Nevins, J. R. 1981. *Cell.* 26:213–20). It was hypothesized that cellular proteins can substitute functionally for E1A in the transactivation of viral promoters (Gaynor, R. B., and A. J. Berk. 1983. *Cell.* 33:683–93; Lieber, A. et al., 1996. *J Virol.* 70:8944–60). Therefore, the first generation Ad E1A/ E1B- adenoviruses are inadequate gene therapy vehicles.

The present invention is an improvement upon the first generation vectors in specifically targeting cells, such as tumor cells, where Ad DNA replication can occur. Ad DNA replication is only initiated upon the production of a critical threshold of early viral proteins which, in turn, is directly dependent on the number of viral genomes present in nuclei of infected cells [(Shenk, T. 1996. *Adenoviridea,* p. 2111–2148. In B. N. Fields, Knipe, D. M., Howley, P. M. (ed.), *Fields Virology,* vol. 2. Lippincott-Raven Publisher, Philadelphia; van der Vliet. 1995. *Adenovirus DNA replication.,* p. 1–31. In a. P. B. W. Doerfler (ed.), The molecular repertoire of adenoviruses, vol. 2. Springer Verlag, Berlin)]. In previous studies, it was demonstrated that de novo DNA synthesis occurs in a number of cell lines and primary cells (including murine hepatocytes) after infection with E1-deleted vectors (Lieber, A. et al., 1996. *J Virol.* 70:8944–60; Nelson, J. E., and M. A. Kay. 1997. *J Virol* 71:8902–7). However, AdE1$^-$ viral DNA replication was not detectable in vivo in mouse livers (Nelson, J. E., and M. A. Kay. 1997. *J Virol.* 71:8902–7). This discrepancy, between primary hepatocytes in vitro and in vivo, prompted us to perform detailed replication studies with E1-deleted vectors in a variety of tumor cell lines. Specifically, we examined the roles of infectivity, tumor suppressor gene status, cell cycling, and presence of serum on vector DNA replication.

Based on the discussion above, a remaining problem in tumor gene therapy involves the inefficient administration of recombinant adenoviral vectors. Efficient adenoviral gene therapy for cancer depends not only on primary gene transfer to a portion of tumor cells, but also on efficient replication and dissemination of the vectors to the surrounding tumor tissue, in order to achieve a complete killing. The invention also addresses this issue.

SUMMARY OF THE INVENTION

This invention provides modified recombinant Ad vectors (e.g., first generation-vectors) undergoing defined homologous recombination in order to create predictably rearranged genomic derivatives in a host cell. Genomic rearrangements can be achieved, for example, by incorporating two inverted repeat (IR) sequences within one vector genome and enabling genomic rearrangement by coinfection with two parental vectors of one type (also referred to herein as a one vector system) (see e.g., Example 1) or by homologous recombination of overlapping regions in two distinct types of parental vectors (with or without IR sequences) and enabling genomic rearrangement only upon coinfection of the host cell with the two distinct parental vectors (also referred to herein as a two vector system) (see e.g., Example 2).

The Ad vectors of the invention allow for tumor-specific gene expression through a recombination mechanism, that is based on the selective replication of the vectors of the invention in tumor cells, as disclosed herein.

The invention also provides methods for viral spread. In the tumor-specific vectors of the invention, viral spread may be facilitated by induction of apoptosis, thereby enhancing virus release from infected cells, infection of surrounding tumor cells and increased tumor cell lysis.

BRIEF DESCRIPTION OF THE FIGURES

FIG. 4: Comparison of the replication and transgene expression kinetics of Ad.IR-BG and Ad.BG FIGS. 5A, 5B, 5C: Expression of HPV E6 and E7 efficiently supports AdE1⁻ DNA replication in vitro and in vivo.

FIG. 10: Replication dependent and tumor specific transgene expression in LOVO cells after infection with Ad.IR-BG.

FIG. 17: A table of viral DNA replication ratios in correlation with development of CPE and p53, pRb, and p16 status of tumor cells.

FIGS. 19A, 19B: AdE1– DNA replication within cells arrested in G2/M by nocodazole.

FIGS. 20A, 20B, 20C, 20D: Replication of AdE1– in cervical carcinoma cells.

DETAILED DESCRIPTION OF THE INVENTION

Definition

Figure 1A:
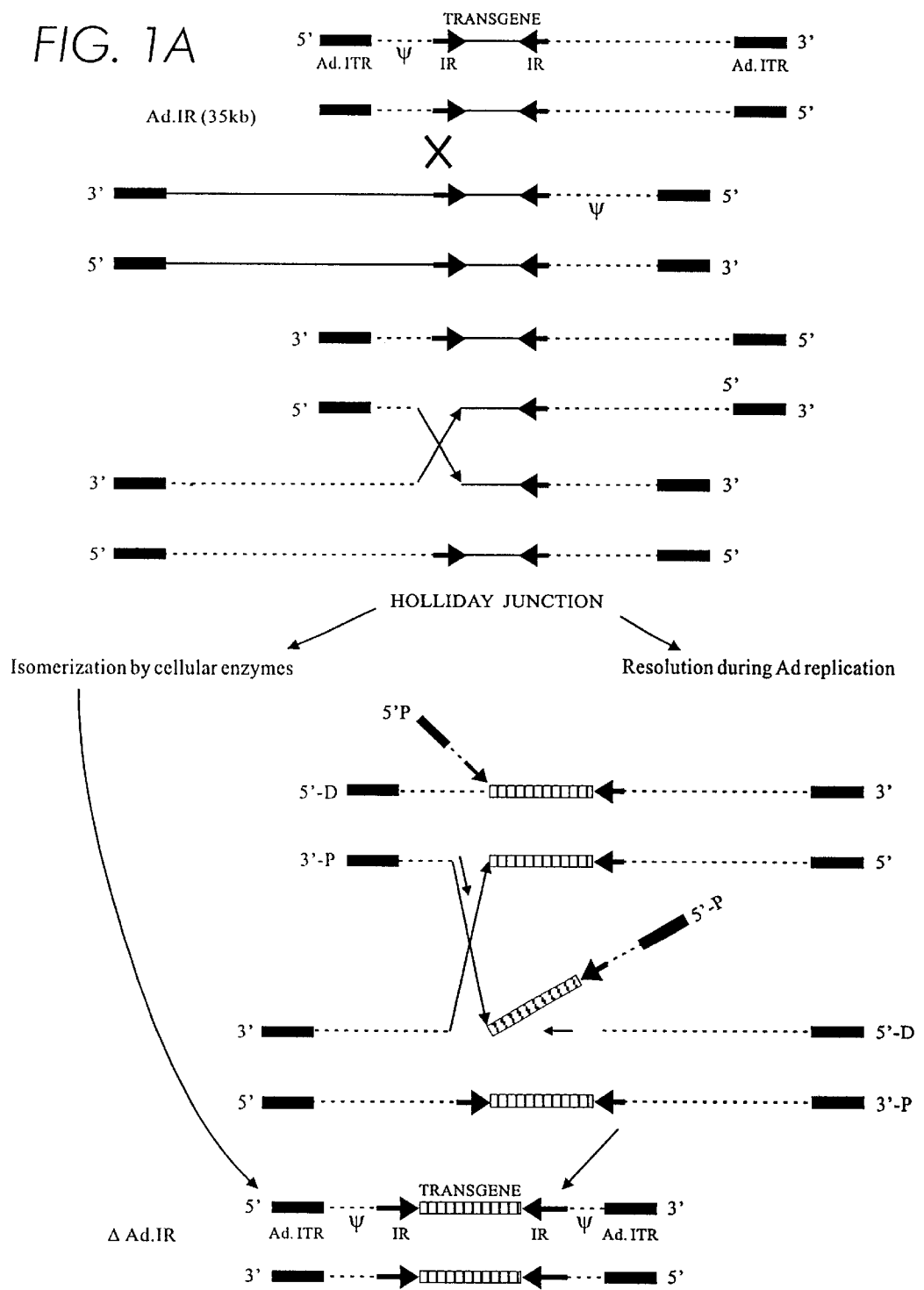
FIGS. 1A, 1B: Hypothetical mechanisms for the formation of a ΔAd.IR genome, replication activated expression system.

Unless defined otherwise, all technical and scientific terms used herein have the same meaning as commonly understood by one of ordinary skill in the art to which this invention belongs. For purposes of the present invention, the following terms are defined below.

As used herein "foreign DNA sequence" means a nucleic acid sequence that is introduced into a vector of the invention encoding all or a portion of a protein of interest. The upper size limit of the foreign DNA sequence is largely dictated by potential stability constraints or size for packaging. The foreign DNA sequence (also referred to here as foreign DNA) can encode any desired protein (protein of interest), preferably one having pharmaceutical or other desirable properties. The foreign DNA sequence may be prepared in accordance with conventional ways, where sequences may be synthesized, isolated from natural sources, manipulated, cloned, ligated, subjected to in vitro mutagenesis, primer repair, or the like.

The term "homologous" as used herein denotes a characteristic of a nucleotide sequence, wherein at least about 70 percent of a region has sequence identity to a second sequence.

The term "homologous recombination" refers to two nucleic acid molecules, each having homologous sequences, where the two nucleic acid molecules cross over or undergo recombination in the region of homology.

The length of homology (overlapping homologous regions) may be selected at the discretion of the practitioner on the basis of the sequence composition and complexity of the foreign DNA sequence and guidance provided in the art (Hasty et al. (1991) Molec. Cell. Biol. 11:5586; Shulman et al. (1990) Molec. Cell. Biol. 10:4466, which are incorporated herein by reference). By way of example, Rubnitz and Subramani (Mol. and Cell. Biol. 4:2253–2258, (1984), describe the minimum amount of homology required for homologous recombination.

The length of overlapping homology can be 100–11,000 base pairs. Preferable lengths for the homology region are, but not limited to: 200 base pairs (bp), 600 bp, 900 bp, 1200 bp, 4500 bp, 7200 bp.

"Tumor specific gene expression" and "tumor specific" is intended to encompass vector gene expression in a tumor cell but it is understood that vector gene expression in normal cells may also occur, albeit at low levels, that may lead to inefficient vector replication and packaging. This low level of vector replication and packaging is considered negligible and background.

The term "first generation adenovirus vectors" or "first generation recombinant adenovirus vectors" is intended to mean any adenovirus vector that has a deletion in one or more E1 and/or E3 gene or genes which renders the adenovirus replication deficient.

The term "non-actively cycling" refers to quiescent cells, which are cells not going through the various stages of the cell cycle pathway [e.g. gap1 (G1), synthesis (S), gap2 (G2) and/or mitosis (M)]. Most often non-actively cycling cells are resting in the G1 or G2 phases.

The term "actively cycling" refers to a cell undergoing a cell cycle, composed of the gap1 (G1), synthesis (S), gap2 (G2) and mitosis (M) phases, in order to replicate.

In order that the invention herein described may be more fully understood, the following description is set forth.

Modified Adenovirus Vectors

The present invention provides novel, modified adenoviral vectors, comprising a foreign DNA sequence flanked by a first and a second inverted repeat sequence, wherein the modified vector lacks an adenoviral gene sequence E1A, E1B, or E3, or lacking any combination of these adenoviral gene sequences. The vector of the present invention includes a pair of adenoviral inverted terminal repeat sequences and at least one adenoviral gene sequence, E1 and E3.

An adenovirus vector is intended to mean all known serotypes of adenovirus e.g., serotypes 1–51.

The adenovirus vector of the invention can be to be packaged within a transduced cell and the packaged vector can transduce another cell. The adenovirus vector of the invention can into the host genome of a transduced cell. The adenovirus vector so integrated is referred to a "integrated viral DNA." The integrated viral DNA is analogous to a retrovirus provirus.

In one embodiment, the first and second inverted repeat sequences have similar sequences. In another embodiment, the first and the second inverted repeat sequences are identical. In another embodiment, the foreign DNA sequence encoded a full-length gene product. In yet another embodiment, the foreign DNA sequence encodes a partial length gene product. The partial length gene product can be an N-terminal portion, or a C-terminal portion, encoded by a 5' portion, or a 3' portion of the foreign DNA sequence, respectively.

In one embodiment, the modified adenoviral vector comprises, in a 5' to 3' orientation: a first adenoviral inverted terminal repeat sequence; a first inverted repeat sequence; a foreign DNA sequence; a second inverted repeat sequence; at least one adenoviral gene sequence, E1 and/or E3; and a second adenoviral inverted terminal repeat sequence.

In a preferred embodiment, the vector comprises, in a 5' to 3' orientation: a first adenoviral inverted terminal repeat sequence oriented in a 5' to 3' direction; a first inverted repeat sequence oriented in a 3' to 5' direction; a foreign DNA sequence oriented in a 3' to 5' direction; a second inverted repeat sequence oriented in a 5' to 3' direction; at least one adenoviral gene sequence, E1 and/or E3; and a second adenoviral inverted terminal repeat sequence oriented in a 3' to 5' direction.

In another embodiment, the modified adenoviral vector comprises a pair of adenoviral inverted terminal repeat sequences, an adenoviral packaging sequence, a promoter sequence, and at least one adenoviral gene sequence, E1 and/or E3. This vector comprises, in a 5' to 3' orientation: a first adenoviral inverted terminal repeat sequence; an adenoviral packaging sequence; a promoter sequence; a first inverted repeat sequence; a foreign DNA sequence; a second inverted repeat sequence; at least one adenoviral gene sequence, E 1 and/or E3; and a second adenoviral inverted terminal repeat sequence. In a preferred embodiment, the vector comprises, in a 5' to 3' orientation: a first adenoviral inverted terminal repeat sequence oriented in a 5' to 3' direction; an adenoviral packaging sequence; a first inverted repeat sequence oriented in a 3' to 5' direction; a foreign DNA sequence oriented in a 3' to 5' direction; a second inverted repeat sequence oriented in a 5' to 3' direction; at least one adenoviral gene sequence, E 1 and/or E3; and a second adenoviral inverted terminal repeat sequence oriented in a 3' to 5' direction.

The modified adenoviral vector of the present invention can replicate in a rapidly cycling cell. A rapidly cycling cell is a cell undergoing G1 (gap 1), S (DNA synthesis), G2 (gap 2), or M (mitosis) in order to replicate the cellular DNA. Rapidly cycling cells include tumor cells. The tumor cell can be derived from any tissue including cervical, colon, lung, or breast tissue.

The tumor cell can be a Burkitt's lymphoma, a nasalpharyngeal carcinoma, a Hodgkins lymphoma, a T cell lymphoma, hepatocellular carcinoma, or apolyoma-induced solid tumor.

The modified adenoviral vector of the present invention undergoes molecular recombination within a cell. Molecular recombination can occur between any two embodiments of the modified adenoviral vectors of the present invention. For example, recombination can occur between two identical vectors, each having a full-length or partial-length foreign DNA sequence. Recombination can occur between two different vectors, including between a vector having a 5' portion of the foreign DNA sequence and a vector having a 3' portion of the foreign DNA sequence.

In a preferred embodiment, the 5' and 3' portions of the foreign DNA sequences have overlapping portions. Recombination can occur between two different vectors, where one vector has a 5' portion of a foreign DNA sequence and the other vector has a 3' portion.

The recombination event can occur between any homologous sequence element along the length of the two vectors undergoing molecular recombination (e.g., homologous recombination). For example, recombination can occur between the inverted repeat sequences on one of the vectors and the inverted repeat sequence on the other vector. Recombination can occur between the overlapping region of homology in the foreign DNA sequences on both vectors.

The two vectors which undergo molecular recombination are termed the "parent" vectors. The vectors resulting from molecular recombination are termed the "resolved" vectors. Molecular recombination between two modified adenoviral vectors of the present invention can generate a resolved vector. The resolved vector has the various vector elements of the parent vectors rearranged in an orientation that differs from the parent vectors. The vector elements include the inverted terminal repeat sequences, packaging sequence, insulator sequence, promoter, inverted repeat sequences, foreign DNA sequence, adenoviral sequences.

The resolved vector can include an additional promoter sequence and upstream of the foreign DNA sequence. For example, in the resolved vector, the second promoter is in a position upstream to the foreign DNA sequence. The promoter which is upstream to the foreign DNA sequence can control transcription of the foreign DNA sequence (e.g., expression of the foreign DNA sequence).

In a more preferred embodiment, two identical parental vectors each including full-length foreign DNA sequences undergo homologous recombination within a cell to generate a resolved vector having the vector elements rearranged in a predictable orientation where the promoter is in a position upstream to the foreign DNA sequence so that the promoter can control transcription of the foreign DNA sequence.

The resolved vectors can act in two ways. Some resolved vectors can integrate into the genome of a host cell. Other resolved vectors can be packaged and enter other cells to replicate and undergo molecular recombination.

In a particular embodiment, the novel Ad vector remains capable of specifically replicating in an actively dividing cell. Moreover, the novel Ad vectors are capable of recombining in an actively cycling cell (referred to herein as "parental vectors"). Alternatively, the parental vectors comprises a foreign DNA sequence encoding a portion of a gene of interest which can encode the N-terminal portion, or the C-terminal portion of the protein of interest.

The parental Ad vectors of the invention, when introduced into a cell, in vitro, ex vivo, or in vivo, replicates in the cell. The Ad vectors can undergo homologous recombination in the cell. Homologous recombination can create predictably rearranged Ad genomic derivatives (referred to herein as resolved vectors). The resolved vectors of the invention are designed to express their resolved foreign DNA sequence within an actively cycling cell; preferably, a tumor cell. The cell can be a human cell or an animal cell.

Genomic rearrangements may be effected, for example, by co-infection with parental vector of one kind (also referred to herein as a one vector system, i.e., wherein one type of parental vector is introduced in a host cell and homologously recombines with another copy) (see e.g., Example 1). Infection with this one vector system provides two inverted repeat (IR) sequences within the genome of a parent vector that enables genomic rearrangement between two parental vectors after infection. The parental vector comprises in a 5' to 3' direction: a 5' Ad inverted terminal repeat (AdITR), or Ad packaging sequence located 3' to the Ad ITR, a heterologous promoter located 3' to the packaging sequence, a 5' IR located 3' to the heterologous promoter, optionally—a bi-directional polyadenylation signal (polyA) located 3' to the 5' IR, a foreign DNA sequence (transgene) located 3' to the 5' IR oriented in the 3'–5' direction, a 3' IR located usptream to the foreign DNA sequence, at least one adenoviral gene sequence required for replication located 3' to the 3' IR, and a 3' ITR located 3' to the viral genes. For convenience, this embodiment is referred to as Ad.IR.

Genomic rearrangements may also be effected, for example, by co-infection with two different parental vectors allowing for homologous recombination between the two parental vectors (a two vector system, i.e., a system having two types of distinct parental vectors, each parental vector carrying a portion of the same foreign DNA sequence, which when introduced in a host cell undergoes homologous recombination to form a resolved vector having the complete foreign DNA sequence) (see e.g., Example 2). In accordance with the invention, the system comprises (1) a first parental Ad vector which comprises an adenovirus left ITR sequence, an adenovirus packaging sequence located 3' to the ITR, a heterologous promoter, a foreign DNA sequence (any recombinant DNA sequence that encodes a portion of a protein), at least one adenoviral gene sequence required for vector replication in a transduced cell (the first parental Ad vector is also referred to herein as Ad.1); and (2) a second parental Ad vector which comprises an adenovirus left inverted terminal repeat (ITR) sequence, at least one adenoviral gene required for vector replication in a transduced cell located 3' to the left ITR, any foreign DNA sequence (any recombinant DNA sequence that encode a portion of a protein) located 3' to adenoviral genes required for vector replication, a polyadenylation stop sequences located 3' to the foreign DNA sequence, an adenovirus packaging sequence located 3' to the polyadenylation stop sequence, and a 3' ITR located 3' to the adenovirus packaging sequence (the second parental Ad virus is also referred to herein as Ad.2).

Optionally, the parental vectors further comprise a stop sequence (or stop site) that ensures that the foreign DNA sequence is transcribed and translated properly. The stop site can be synthetic or of natural origin. Examples of stop sites include, but are not limited to, a polyadenylation stop site from the SV40 virus and a synthetic bi-directional transcriptional stop site. Typically, the bi-directional polyadenylation stop site arrests transcription of DNA sequences downstream from the transgene.

In accordance with the invention, the promoter can be tissue-specific, tumor-specific, non-tissue specific, inducible or constitutive. An example of a suitable non-specific promoter is a viral promoter that includes the Rous Sacroma Virus (RSV), CMV, HSV and HPV promoters. Although a tumor specific promoter is not necessary it can be employed as a heterologous promoter to increase tumor specificity.

To shield a tumor specific promoter from interference by adenoviral cis-acting DNA elements, an insulator DNA element can be inserted in the vector. Preferably, insertion is 3' of the packaging signal and 5' of the heterologous promoter. Suitable insulator DNA elements include, but are not limited to, a globin DNA element (e.g. chick globin DNA element) and gypsy DNA element (e.g. fly gypsy DNA element).

In accordance with the invention, a 3' IR sequence that does not interfere with the foreign gene transcription or translation can be included in the parental vector of the invention to improve the transcription from the resolved vector (infra). Suitable IRs include the 5' untranslated regions of efficiently translated mRNAs (e.g. housekeeping genes) with a minimum size of 100 bp, internal ribosome entry sites or intron sequences with a minimum size of 100 bp.

Preferably, the first and second inverted repeat sequences in the vector are the same and are in inverted orientation with respect to each other. These sequences can be between 100–3,000 base pairs. Preferably, the inverted repeat sequences are excisable. This provides more efficient transcription of the transgene. Examples of inverted repeat sequences include a β-globin intron which does not contain a transcription or translational stop site, but contains a splice acceptor and donor site.

In accordance with the practice of the one vector system (Ad.IR) of the invention, the foreign DNA sequence can be oriented 3'–5' (in reverse orientation) and requires a recombination event to place a promoter in position to drive transcription of the transgene. The promoter (e.g. a heterologous promoter) allows transcription of the transgene from the same or different species in a host cell. Any transgene that is desired to be expressed can be employed such as a reporter gene or effector (or therapeutic) gene. Examples of foreign DNA sequence include, but are not limited to, pro-apoptotic genes, cytolytic genes, suicide genes (such as oncogenes, tumor suppressor genes, toxins, or prodrug enzymes).

Examples of pro-apoptotic or cytolytic gene products include a dominant negative Iκ-B, caspase-3, caspase-6, and a fusion protein containing a toxic moiety and the HSV VP22 protein.

Suicide genes are gene sequences, the expression of which produces a protein or agent that inhibits tumor cell growth or promotes tumor cell death. Suicide genes include genes encoding enzymes (e.g., prodrug enzymes), oncogenes, tumor suppressor genes, genes encoding toxins, genes encoding cytokines, growth factors, or a gene encoding oncostatin.

A purpose of the transgene can be to inhibit the growth of, or kill, the cancer cell or produce agents which directly or indirectly inhibit the growth of, or kill, the cancer cells.

Suitable prodrug enzymes include thymidine kinase (TK), human β-glucuronidase, xanthine-guanine phosphoribosyltransferase (GPT) gene from *E. Coli* or *E. Coli* cytosine deaminase (CD), or hypoxanthine phosphoribosyl transferase (HPRT). In these cases, a substrate can be administered that is metabolized by the expression product of the gene, e.g., TK or CD gene.

Examples of oncogenes and tumor suppressor genes include neu, EGF, ras (including H, K, and N ras), p53, p16, p21, Retinoblastoma tumor suppressor gene (Rb), Wilm's Tumor Gene Product, Phosphotyrosine Phosphatase (PTPase), and nm23.

Examples of suitable toxins includes Pseudomonas exotoxin A and S; diphtheria toxin (DT); *E. coli* LT toxins, Shiga toxin, Shiga-like toxins (SLT-1, -2), ricin, abrin, supporin, and gelonin.

Suitable cytokines include interferons, interleukins, tumor necrosis factor (TNF) (Wong G, et al., Human GM-CSF: Molecular cloning of the complementary DNA and purification of the natural and recombinant proteins. Science 1985, 228:810); WO9323034 (1993); Horisberger M A, et al., Cloning and sequence analyses of cDNAs for interferon- and virus-induced human Mx proteins reveal that they contain putative guanine nucleotide-binding sites: functional study of the corresponding gene promoter. Journal of Virology, 1990 March, 64(3):1171–81; Li Y P et al., Proinflammatory cytokines tumor necrosis factor-alpha and IL-6, but not IL-1, down-regulate the osteocalcin gene promoter. Journal of Immunology, Feb. 1, 1992, 148(3):788–94; Pizarro T T, et al. Induction of TNF alpha and TNF β gene expression in rat cardiac transplants during allograft rejection. Transplantation, 1993 August, 56(2):399–404). Breviario F, et al., Interleukin-1-inducible genes in endothelial cells. Cloning of a new gene related to C-reactive protein and serum amyloid P component. Journal of Biological Chemistry, Nov. 5, 1992, 267(31):22190–7; Espinoza- Delgado I, et al., Regulation of IL-2 receptor subunit genes in human monocytes. Differential effects of IL-2 and IFN-gamma. Journal of Immunology, Nov. 1, 1992, 149(9):2961–8; Algate P A., et al., Regulation of the interleukin-3 (IL-3) receptor by IL-3 in the fetal liver-derived FL5.12 cell line. Blood, May 1, 1994, 83(9):2459–68; Cluitmans F H, et al., IL-4 down-regulates IL-2-, IL-3-, and GM-CSF-induced cytokine gene expression in peripheral blood monocytes. Annals of Hematology, June 1994, 68(6):293–8; Lagoo, A S, et al., IL-2, IL-4, and IFN-gamma gene expression versus secretion in superantigen-activated T cells. Distinct requirement for costimulatory signals through adhesion molecules. Journal of Immunology, Feb. 15, 1994, 152(4):1641–52; Martinez O M, et al., IL-2 and IL-5 gene expression in response to alloantigen in liver allograft recipients and in vitro. Transplantation, May 1993, 55(5):1159–66; Pang G, et al., GM-CSF, IL-1 alpha, IL-1 β, IL-6, IL-8, IL-10, ICAM-1 and VCAM-1 gene expression and cytokine production in human duodenal fibroblasts stimulated with lipopolysaccharide, IL-1 alpha and TNF-alpha. Clinical and Experimental Immunology, 1994 June, 96(3):437–43; Ulich T R, et al., Endotoxin-induced cytokine gene expression in vivo. III. IL-6 mRNA and serum protein expression and the in vivo hematologic effects of IL-6. Journal of Immunology, Apr. 1, 1991, 146(7):2316–23; Mauviel A, et al., Leukoregulin, a T cell-derived cytokine, induces IL-8 gene expression and secretion in human skin fibroblasts. Demonstration and secretion in human skin fibroblasts. Demonstration of enhanced NF-κ β binding and NF-κ β-driven promoter activity. Journal of Immunology, Nov. 1, 1992, 149(9):2969–76).

Growth factors include Transforming Growth Factor-α (TGFα) and β (TGFβ), cytokine colony stimulating factors (Shimane M, et al., Molecular cloning and characterization of G-CSF induced gene cDNA. Biochemical and Biophysical Research Communications, Feb. 28, 1994, 199(1):26–32; Kay A B, et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. Journal of Experimental Medicine, Mar. 1, 1991, 173(3):775–8; de Wit H, et al., Differential regulation of M-CSF and IL-6 gene expression in monocytic cells. British Journal of Haematology, 1994 February, 86(2):259–64; Sprecher E, et al., Detection of IL-1 β, TNF-α, and IL-6 gene transcription by the polymerase chain reaction in keratinocytes, Langerhans cells and peritoneal exudate cells during infection with herpes simplex virus-1. Archives of Virology, 1992, 126(1–4):253–69).

In one embodiment of the invention, the genes-for-replication of the adenovirus vector in the transduced cell include E1, E2, and E4. In another embodiment of the invention, the genes-for-replication of the adenovirus vector in the transduced cell include E2, E3, and E4. In another embodiment of the invention, the genes-for-replication of the adenovirus vector in the transduced cell include E2 and E4. It is also contemplated in this invention that any or all of these vectors (i.e., first generation adenovirus vectors) can be used in combination (at the same time) to transduce cells. For example, a transduced cell is infected with three distinct Ad.IRs that include E1, E2, and E4 genes-for-replication, or E2, E3 and E4 genes-for replication, or E2 and E4 genes-for-replication.

In another embodiment, the vectors of the invention further comprise a selectable marker. The selectable marker may be any marker known in the art, for instance a gene coding for a product which confers antibiotic resistance to the cell or which complements a defect of the host. Cells surviving under these conditions will be cells containing the vector comprising the DNA construct of the invention.

In another example, the selectable marker can be the herpes simplex virus thymidine kinase (HSV-tk) gene since the presence of the thymidine kinase (tk) gene may be detected by the use of nucleoside analogs, such as acyclovir or gancyclovir, for their cytotoxic effects on cells that contain a functional HSV-tk gene. The absence of sensitivity to these nucleoside analogs indicates the absence of the thymidine kinase and, therefore, where homologous recombination has occurred, a crossover event has also occurred.

Examples of additional suitable detectable markers include, but are not limited to, prokaryotic β-galactosidase, radioisotope concentrator, alkaline phosphatase, and green-fluorescent protein.

Resolved Vectors Made by Homologous Recombination

Resolved vectors can be generated using the parental vectors of the invention. For example, the vectors of the invention can be introduced into a host cell (preferably a tumor cell) by well-known methods, such as infection. After infection, Ad DNA replication occurs specifically in cycling cells such as tumor cells. After replication the resolved Ad vector of the invention can integrate into the genome of the transduced cell. Alternatively, the replicated Ad vector can be packaged.

For example, in the one vector system, Ad DNA replication allows a parental Ad vector to homologously pair with another copy of the vector in the host cell. The parental vectors then homologously recombine so as to generate a resolved vector (e.g., ΔAd.IR) capable of expressing the resolved foreign DNA sequence and incapable of being efficiently packaged into virions. This resolved vector (e.g., ΔAd.IR) contains the complete foreign DNA sequence, an IR sequence flanking the foreign DNA sequence on both the 5' and 3' sides, two inversely oriented copies of the parental vector's 5' terminus flanking the 5' and 3' IR, respectively, plus a promoter 5' to the foreign DNA sequence in 3' 5' orientation capable of driving transcription of the foreign DNA sequence. In an embodiment, the 5' terminus comprises the Ad ITR, the packaging signal 3' of the Ad ITR and all sequences located 3' to the packaging signal and 5' to the 5' IR. Preferably, adenovirus genes for replication are not in the resolved vector.

As another example, in the two vector system, Ad DNA replication allows the two parental Ad vectors to homologously pair with one another and undergo homologous recombination in overlapping homologous regions of the transgene thereby generating a resolved vector. The resolved vector has a complete foreign DNA sequence capable of being expressed in the host cell.

The resolved vector (e.g., ΔAd.1-2) will comprise the complete transgene. By complete transgene it is intended that the transgene is capable of expressing a protein of interest. Also, the resolved vector comprises copies of a portion of parental vectors'5' and 3' termini. The portion of the parental 5' termini present in the resolved vector comprises the 5' Ad ITR, the packaging signal located 3' to the Ad ITR and the heterologous promoter located 3' to the packaging signal. The portion of the parental 3' termini present in the resolved vector comprises, the polyadenylation stop site located 3' to the transgene, an adenovirus packaging sequence located 3' to the polyadenylation site, and the 3' ITR located 3' to the packaging signal. Preferably, adenovirus genes for replication are not in the resolved vector.

Specific functional elements of the resolved vectors include the heterologous promoter that initiates expression of the transgene due to the established conjunction with the transgene's 5' terminus. Optionally—a bi-directional polyA that prevents formation of anti-sense RNA from the parental vector is also included. Efficient formation of the resolved vector will only occur upon DNA replication of the parental vector. This system allows for replication dependent gene expression as well as possibly tumor specific gene expression.

The portion of foreign DNA sequence that undergoes recombination may generally be in a range of between 100 bp to about 11000 bp in length. Preferable lengths for the homology region are, but not limited to: 200 base pairs (bp), 600 bp, 900 bp, 1200 bp, 4500 bp, 7200 bp. The region that undergoes recombination may include a portion of the coding region, where the coding region may be comprised only of an open reading frame or a combination of exons and introns.

In order to prepare the vectors of the invention, it will be preferable to know the sequence that undergoes homologous recombination. The size of the homologous regions will be determined by the size of the known sequence.

Once the vectors of the invention transduce an actively cycling cell they can replicate and either (1) be packaged or (2) undergo homologous recombination and express its transgene. In the first case, the parental vectors are efficiently packaged, exit the host and go on to transduce other local cells, e.g. actively cycling cells or metastatic cells. In the second case, the parental vectors replicate and undergo homologous recombination to produce a resolved vector able to express its transgene. The resolved vector is packaged at a much lower efficiency. These two features of the invention allow the vectors to spread and transduce cells within a localized area such as a tumor, as well as to spread and transduce cells in dispersed sites such as metastatic sites, while expressing its transgene in all transduced cells.

Uses of the Modified Vectors of the Invention

The Ad vectors of the invention can be used in methods for selectively transducing cells (such as tumor cells). Transduced cells undergoing cell cycling can then express a desired resolved foreign DNA sequence in the vector so as to directly or indirectly ameliorate a diseased state. Such methods include gene therapy methods.

The vectors of the invention can express a resolved foreign DNA sequence (e.g., a transgene) predominantly in tumor cells thus allowing expression of the transgene in tumor cells, such as cervical, lung, liver, breast, colon, prostate, bladder and pancreatic tumor cells.

In one embodiment, this involves methods for viral spreading. The method comprises administering an Ad vector of the invention (e.g., a parental vector) to a subject and permitting infection of the virus in the host cells of the subject. Infection results in transduced cells that produce packaged Ad viruses that can exit and infect other cells, therefore producing viral spread. The presence of an apoptotic gene in the vector induces killing of the transduced cell which allows some Ad vectors to be packaged and exit the cell, so that viral spread can occur.

The Ad vectors of the invention may be administered to a subject in an amount and for a time (e.g. length of time and/or multiple times) sufficient to transduce cells in the subject.

Dosage of a Ad vector is dependant upon many factors including, but not limited to, the type of cell or tissue affected, the type of disease being treated, the severity of the disease, a subject's health and response to the treatment. Accordingly, the dosages can vary depending on each subject and the mode of administration.

Advantages of the Invention

A significant advantage of the invention is that it provides a means to achieve gene expression specifically in situations of rapidly cycling cells, i.e., in tumor cells. Tumor specific expression of cytotoxic or pro-apoptotic genes using this vector system can be used to treat a variety of cancers, e.g., where deregulated cell cycle control supports first generation adenovirus replication.

The invention generates a functional promoter/gene constellation only upon viral DNA replication and thus represents a new principle of selective transcriptional activation, which can be applied to any type of conditionally replicating Ad vector.

In contrast to the invention, most of the current Ad based tumor gene therapy protocols utilize potential tumor specific promoters to express therapeutic genes (Zhang, W. W. 1999 Cancer Gene Ther 6, 113–38; Parr, M. J. et al. 1997 Nat Med 3, 1145–9). However, the application of heterologous promoters in Ad vectors is problematic because their activity and specificity is often affected by viral enhancers and promoters present in the vector genome (Babiss, L. E., et al. 1986 Mol Cell Biol 6, 3798–806; Ring, C. J., et al. 1996 Gene Ther 3, 1094–103, Steinwaerder, D. S. and A. Lieber, 2000, Gene Therapy 7:556–67) or by host cellular components. The invention generates a functional promoter/gene constellation only upon viral DNA replication and thus represents a new principle of selective transcriptional activation, which can be applied to any type of conditionally replicating Ad vector.

The following examples are presented to illustrate the present invention and to assist one of ordinary skill in making and using the same. The examples are not intended in any way to otherwise limit the scope of the invention.

EXAMPLE I

This example shows tumor specific gene expression using the replication activated Ad vector of the invention: a recombinant Ad vector which comprises: an adenovirus left inverted terminal repeat sequence; an adenovirus packaging sequence located 3' to the left inverted terminal repeat sequence; a promoter sequence located 3' to the adenovirus packaging sequence; a pair of first and second inverted repeat sequences wherein the first inverted repeat sequence is located 3' to the promoter sequence and the second inverted repeat sequence is located upstream to a foreign DNA sequence, the foreign DNA sequence in 3'–5' orientation located 3' to the first inverted repeat sequence; a gene or genes for replication of the first generation Ad vector in a transduced cell, located 3' to the second inverted repeat sequence; and an adenovirus right inverted terminal repeat sequence located 3' to the gene or genes for replication of the adenovirus vector in the transduced cell (Steinwaerder, D, et. Al., 2001 Nature Medicine 7:2; 240–243).

Methods

Tissue culture: Cell lines were obtained from ATCC (Manassas, Va.) unless otherwise indicated. 293 (Microbix, Toronto, Canada), HeLa (ATCC # CCL-2), and SK-Hep1 cells (HTB-52) were grown in Dulbecco's Modified Eagle Medium (DMEM), containing 10% Fetal Bovine Serum (FBS), supplemented with 2 mM L-Glutamine (Glu), 100 U/ml Penicillin (P), and 100 mg/ml Streptomycin (S). SiHa (ATCC# HTB-35) and Caski (ATCC # CRL-1550) were grown in DMEM containing 15% FBS, Glu/PS. LOVO cells (ATCC # CCL-229) were grown in F12K media supplemented with 15% FBS, Glu/PS. Cells were maintained at 37° C. and 5% CO2. Cells for transplantation were cultured on untreated petri dishes to minimize adherence, harvested as a single cell suspension with 0.6 mM EDTA and washed twice with DMEM. X-gal staining of adherent cells was performed as described earlier (Lieber, A., et al. 1996 J Virol 70, 8944–60). βGal activity was quantified luminometrically using the βGal reporter gene assay kit (Boehringer Mannheim, Mannheim, Germany). Cytopathic effect assay was based on staining with crystal violet. The medium was removed and the cells were fixed for 3 min in 3.7% para-formaldehyde at room temperature. Next, cells were washed with PBS and incubated for 3 min in 1% crystal violet in 70% ethanol. After staining, cells were rinsed 3 times with water and air-dried for photography. Plaque assays on 293 cells were performed as described elsewhere (Lieber, A., et al. 1996 J Virol 70, 8944–60).

pAd.IR-βGal vector: The 417 bp SV40 polyadenylation signal (SV40pA) was cut out of pREP4 (Invitrogen, Carlsbad, Calif.) by XhoI/SalI digestion and inserted into the XhoI site of pBluescript KS(−) (Stratagene, La Jolla, Calif.) resulting in pBSSV40pA. The 3.4 kb βGal gene was inserted into the blunted BamHI sites of pBSSV40pA resulting in pbGalSV40pA. The 660 bp intron II of the rabbit b globin locus was excised from pSG5 (Stratagene, La Jolla, Calif.) by ClaI/EcoRI digestion and inserted into the corresponding sites of pBluescript KS(−) resulting in pBSbII. A 3.9 kb fragment containing the βGal gene linked to the SV40 pA was taken from pbGalSV40 pA by SpeI/Asp718 digestion, blunted by T4 polymerase, and inserted into the SmaI site of pBSbII producing pbGalSV40bII. A second copy of the bII intron was excised from pSG5 by AvrII/BamHI digestion and inserted into the XbaI and BamHI sites of pbGalSV40bII resulting in pbGalSV40bII2. The 630 bp RSV promoter was taken from pREP4 by SalI/XhoI digestion and inserted into the XhoI site of a modified pDE1sp1A producing pHVRSV. To generate the viral shuttle vector pAdIR-BG, the 5.3 kb bGalSV40bII2 cassette was cut out of pbGalSV40bII2 by NotI/SalI digestion, blunted by T4 polymerase and inserted into the EcoRV site of pHVRSV. The 4.6 kb bGalSV40bII cassette was taken from pbGalSV40bII by XbaI/XhoI digestion and inserted into the SalI and XbaI sites of pHVRSV resulting in pAdCo. Both shuttle vectors were linearized by XmnI digestion and cotransfected with pBHG10 into 293 cells to produce the AdE1⁻ vectors Ad.IR-BG and Ad.Co (FIGS. 2II and 2III). To assess contamination of AdE1⁻ vector preparations with E1⁺ replication competent Ad, PCR analysis for recombination E1⁺ adenovirus was performed according to a protocol described elsewhere (Zhang, W. W., et al. 1995 Biotechniques 18, 444–7). This assay can detect one E1A+ genome in $10^9$ pfu of recombinant virus. The following primers were used for the E1A-PCR: AAGGATCCGCCAGCCATGGAGGAGTTTGTGTTAGATTAT (SEQ ID NO: 1) as 5' primer and AGATCTCTAACTAACGGGACTGTAGACAAACATGCCAC (SEQ ID NO: 2) as 3' primer. The PCR Conditions used were: 2.5 U Taq-polymerase (Gibco BRL, Gaithersburg, Md.) in 50 ml reaction volume, 5% DMSO, and 2.5 mM MgCl2. 30 cycles of 1 min denaturation (95° C.), annealing (55° C.), and elongation (72° C.) were carried out.

The presence of bacterial endotoxin in virus preparations was excluded by tests described earlier (Lieber, A. et al. 1997 J Virol 71, 8798–807).

Activation of transgene expression from AdE1− vectors upon viral DNA replication: Inverted repeats (IRs) inserted into the E1 region of AdE1− vectors could efficiently mediate predictable genomic rearrangements depending on viral DNA replication (Steinwaerder, et al. 1999 J Virol 73, 9303–13). To utilize this finding for a replication dependent expression system, the vector Ad.IR-BG, which contains the βGal gene oriented towards a RSV promoter (FIG. 2II), was constructed. We postulated that inverse homology regions flanking the βGal gene would mediate genomic rearrangements bringing the transgene into conjunction with the promoter depending on vector replication. As a control, a vector containing only one homology element (Ad.Co) was constructed(FIG. 2III). FIG. 2II shows the formation of the predicted rearranged genomes (ΔAd.IR-BG) after infection of cervical carcinoma cell lines with Ad.IR-BG but not after infection with Ad.Co. The appearance of ΔAd.IR-BG was inhibited in the presence of hydroxyurea (HU), which blocks adenoviral DNA replication but not protein synthesis (Sussenbach, J. S. & van der Vliet, 1973 P. C. Virology 54, 299–303). The same experimental scheme was used to demonstrate replication dependent activation of βGal expression from ΔAd.IR-BG genomes (FIGS. 3A, 3B). In SiHa and Caski cells with Ad.IR-BG, X-Gal positive cells appeared only upon vector DNA replication, whereas a vector containing the βGal gene under control of the RSV promoter (Ad.BG) (FIG. 2I) expressed βGal constitutively in both HU treated or untreated cells. As expected, no βGal expression was observed after infection with Ad.Co. However, some background expression was detected in Ad.IR-BG and Ad.Co infected HeLa cells independent of ΔAd.IR-BG formation. βGal enzyme activity was 1 to 3 orders of magnitude higher in Ad.IR-BG infected cells in the absence of HU than in cells where viral replication was blocked by HU, depending on the cell type Replication assays: For the generation of methylated Ad.BG, Ad.E6, and Ad.E7 vectors, viruses were amplified in 293-PMT cells expressing the prokaryotic PaeR 7 methyl transferase (PMT) (Nelson, J. E. & Kay, M. A. 1997 J Virol 71, 8902–7). Cells were infected with methylated Ad as described in the text and figure legends. To isolate cellular/viral DNA, cells were treated with 0.05% Trypsin/0.53 mM EDTA and recovered by centrifugation. DNA extraction was performed as described earlier (Lieber, A., et al. 1996 J Virol 70, 8944–60). The DNA concentration was measured by photospectrometry. To determine the ratio of replicated versus non-replicated viral DNA, the extracted total DNA was digested with HindIII and XhoI and subjected to agarose gel electrophoresis followed by Southern blotting (Lieber, A., et al. 1996 J Virol 70, 8944–60). The blots were probed using an 8 kb HindIII fragment of the Ad5 genome (bp 18319 to bp 26328).

Double digestion with HindIII and XhoI yields clearly distinguishable DNA fragments specific for demethylated (replicated) and methylated (non-replicated) viral DNA, because methylation of the viral genome during amplification in 293-PMT cells blocks the XhoI site at Ad5 bp 24796. Therefore, only progeny viral DNA can be cut by XhoI at bp 24796 resulting in two detectable fragments of 1.5 kb and 6.5 kb after HindIII and XhoI digest.

The following experiments show that the Human Papilloma Virus genes E6 and E7 efficiently support the replication of an E1 deleted adenovirus vector in vivo and in vitro.

Plasmid constructs and Vectors: pCMVE6/E7: The HPV16 E6 and E7 reading frames were taken from pLXSNE6/E7 (Halbert, C. L., et al. 1991 J Virol 65, 473–8). The 300 bp long HPVE7 gene was released from pLXSNE6/E7 by BamHI digestion and inserted into the BamHI site of pcDNA3.1 (Invitrogen, Carlsbad, Calif.) resulting in pCMVE7. The 480 bp long HPVE6 gene was cut out of pLXSNE6/E7 by BstYI digestion. After T4 polymerase mediated fill in of the 5' overhang, the fragment was inserted into the EcoRV site of pcDNA3.1 resulting in pCMVE6.

pAdE6/E7 and Ad.E6/E7: The expression cassettes containing the CMV promoter, the E6 or E7 gene and the bovine growth hormone polyadenylation signal (bpA) were excised from pCMVE6 and pCMVE7 by SalI/DraIII digestion. After T4 polymerase mediated blunting of the DraIII 3' overhand, the fragments were inserted into a modified pDE1sp1A opened with SalI and EcoRV resulting in pAdE6 and pAdE7, respectively. The shuttle vectors pAdE6 and pAdE7 were linearized by XmnI digestion and cotransfected with pJM17 (Bett, A. J., et al. 1994 Proc Natl Acad Sci U S A 91, 8802–6) into 293 cells to create the Ad.E1− vectors Ad.E6 and Ad.E7. The construction of Ad.RSVbGal has been previously described (Stratford-Perricaudet, L. D., et al. 1992 J Clin Invest 90, 626–30).

Immunoprecipitation: HPV E6 and E7 proteins were 35S-labeled and purified as described in the Oncogene/Calbiochem (Calbiochem, Cambridge, Mass.) immunoprecipitation manual. For immunoprecipitation, a 1:1 mixture of monoclonal and polyclonal anti HPVE6 and HPVE7 antiserum (St. Cruz Biotechnology, St. Cruz, Calif.) was used. The protein samples were separated in a 12% polyacrylamide gel. The gel was treated with the autoradiography enhancer Entensify (NEN Research Systems, Boston, Mass.), dried, and exposed to Kodak X-OMAT AR imaging film (Eastman Kodak, Rochester, N.Y.). FIG. 5

Figure 1B:
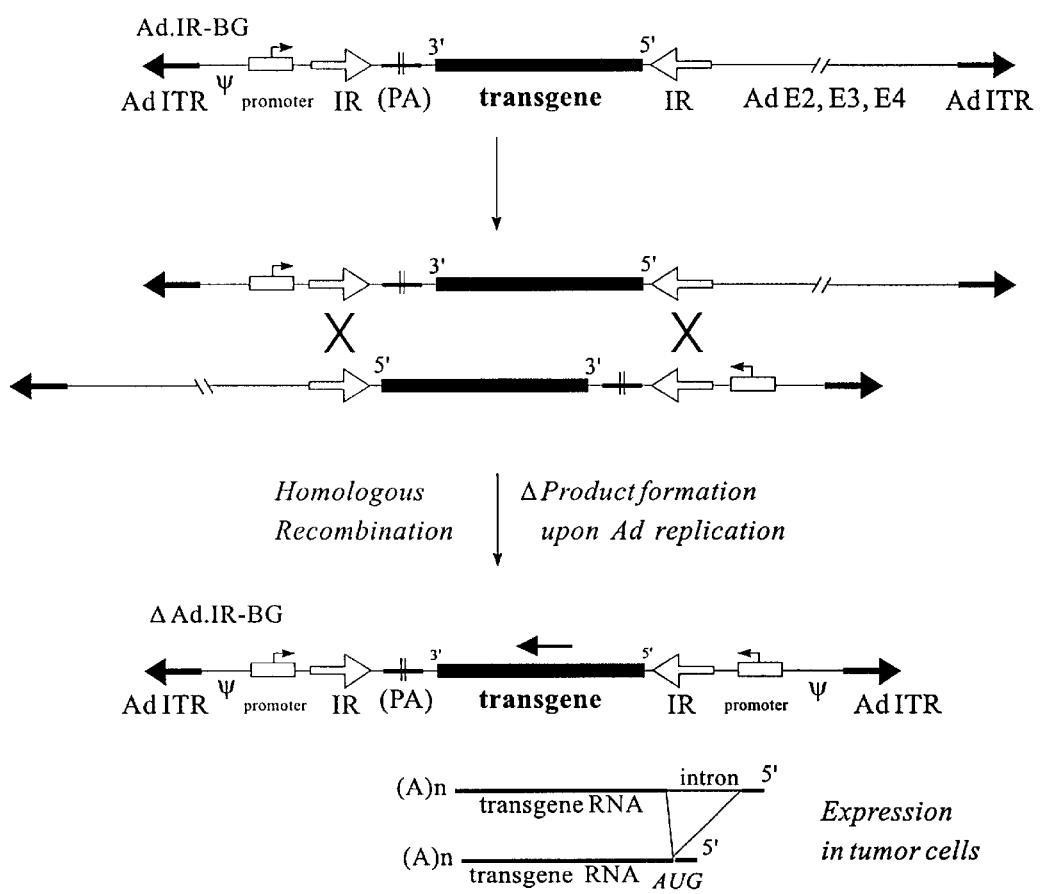

Discussion:

According to an accepted model for general recombination, a recombination process could begin with the pairing of homologous regions within the IR elements of two double-stranded Ad genomes containing inverted repeats (Ad.IR; FIGS. 1A, 1B). Then, cellular recombination enzymes would mediate the exchange of a single strand between the two double-stranded viral genomes resulting in a Holliday-junction. This structure could isomerize by undergoing a series of rotational movements as described for the classical Holliday-resolution model (FIG. 1A). Alternatively, the Holliday-structure could be resolved during Ad replication. The synthesis of a daughter strand (5'-D) is associated with the displacement of one parental strand (5'-P) and could occur along the crossed strands. When two oppositely moving displacement forks meet at the crossover, the two crossed parental strands will no longer be held together and separate resulting in partially duplex and partially single-stranded molecules. The synthesis is then completed on the displaced parental strand. A similar dissociation mechanism is described for Ad2 replication. One of the recombination products has the structure of ΔAd.IR genomes. Theoretically, a second double-stranded product with a length of ~67 kb should also form. It is not possible to demonstrate the presence of this product by Southern-Blot. This product was apparently not efficiently generated. Its large size would require extremely long periods of replication (>40 min). Based on the predicted structure, the 67 kb product would lack packaging signals. Besides this, the large size of this product would prevent packaging. The figure shows only the pairing and the cross-exchange for one IR pair. With the same likelihood, recombination can occur between the other IR-pair resulting in identical products. To simplify the Holliday resolution model by Ad replication, only DNA synthesis initiated from one genome end is shown.

A wide variety of cell lines derived from tumors other than cervical carcinomas can also efficiently support AdE1− DNA. Furthermore, in tumors associated with DNA viruses (EBV, HBV, polioma virus etc.), viral gene products can functionally substitute for adenoviral E1 proteins (Gjorup, O. V., et al. 1994 Proc Natl Acad Sci U S A 91, 12125–9; Schaack, J., et al. 1996 Virology 216, 425–30; Tevethia, M. J. & Spector, D. J. 1984 Virology 137, 428–31; Tevethia, M. J. & Spector, D. J. 1989 Prog Med Virol 36, 120–90). Consequently, the presented replication activated expression system should allow for specific transgene expression in a variety of tumor types. Representatively, we demonstrated this in liver metastases derived from a colon carcinoma cell line.

The concept of selective Ad replication as an anti-tumor approach has been extensively studied using an AdE1A$^+$ vector carrying deletions in E1B (Heise, C. et al. 1997 Nat Med 3, 639–45; Wildner, O. et al. 1999 Gene Ther 6, 57–62; Heise, C. C., et al. 1999 Cancer Res 59, 2623–8; Bischoff, J. R. et al. 1996 Science 274, 373–6). The tumor specificity of this vector is controversial (Rothmann, T., et al. 1998 J Virol 72, 9470–8; Vollmer, C. M. et al. 1999 Cancer Res 59, 4369–74; Turnell, A. S., et al. 1999 J Virol 73, 2074–83; Hay, J. G. et al. 1999 Hum Gene Ther 10, 579–90; Harada, J. N. & Berk, A. J. 1999 J Virol 73, 5333–44; Hall, A. R., et al. 1998 Nat Med 4, 1068–72; Goodrum, F. D. & Ornelles, D. A. 1998 J Virol 72, 9479–90) and, due to E1 expression, side effects on normal tissues can not be excluded.

In summary, first-generation, E1 deleted adenovirus vectors can specifically replicate in tumors cells. For example, the intrinsic property of cervical carcinoma cells to express HPV E6/E7 proteins supports replication of E1 deleted Ad vectors whereas most normal cells do not. Based on these finding the novel Ad.IR vector allows predictable genomic rearrangements and replication activated transcription in tumor cells.

A replication activated expression system was demonstrated. A summary of replication activated adenovirus vectors with tumor-specific gene expression that require recombination between IR sequences present in one vector is shown (FIGS. 1A, 1B).

Figure 2:
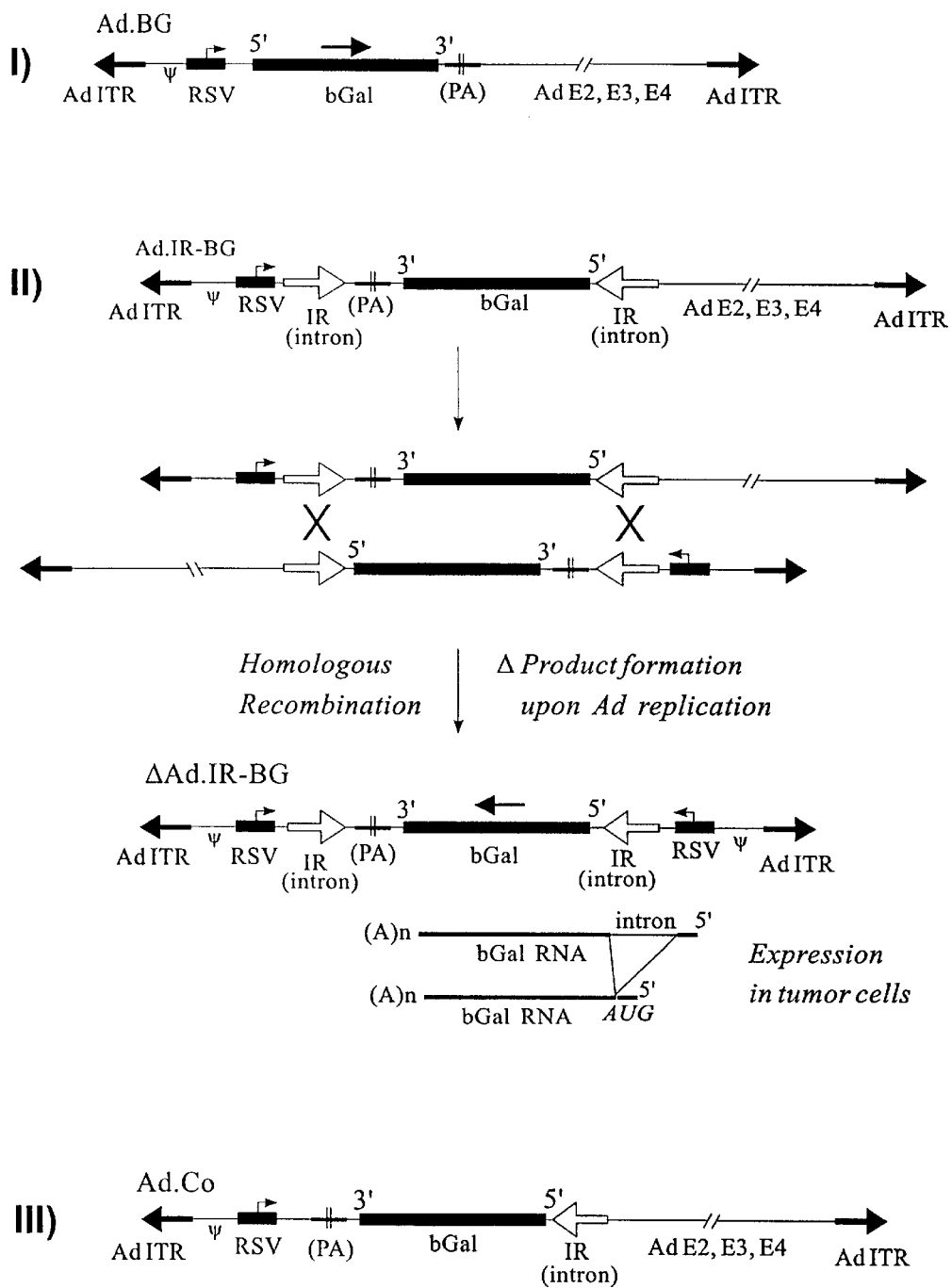
FIGS. 2I, 2II, 2III: The structure of Ad vectors and a scheme of replication activated transgene expression.
Figure 3A:
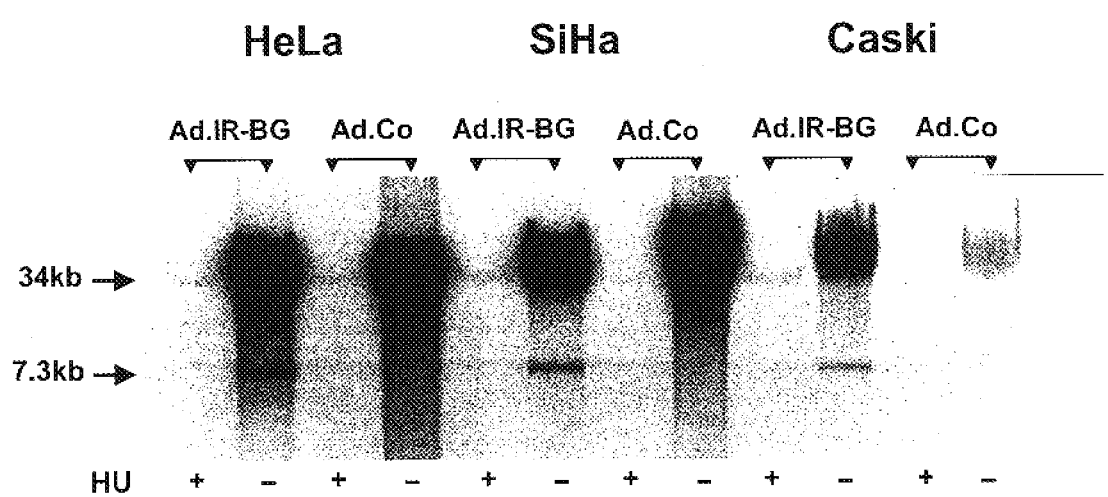
FIGS. 3A, 3B: Activation of transgene expression in vitro upon Ad vector replication.
Figure 3B:
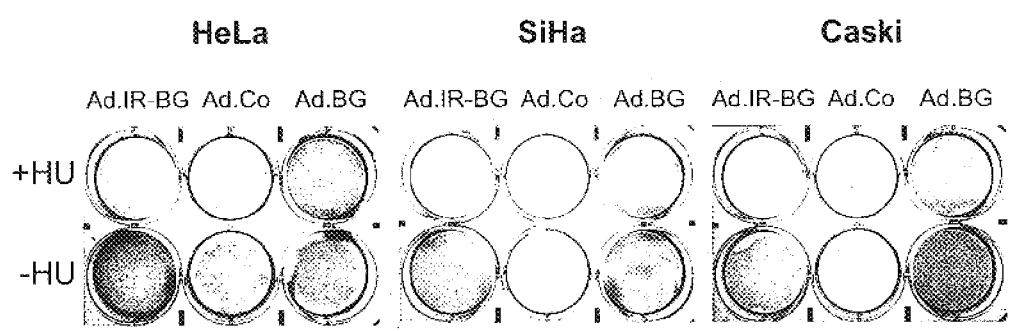

The structure of Ad vectors is shown and the principle of replication activated transgene expression is hypothesized (FIG. 2). Ad.BG comprises the prokaryotic βGal gene under constitutive control of the RSV promoter inserted into the E1 region (FIG. 2I). The parental vector Ad.IR-BG contains the βGal gene flanked by two inverse homology elements (FIG. 2II). The βGal gene is directed in 3'–5' orientation, oriented towards the RSV promoter located downstream of the Ad packaging signal (ψ) and the viral inverted terminal repeats (Ad ITR). The homology elements (IR) mediate the formation of genomic derivatives (ΔAd.IR-BG), containing the promoter in a transcriptionally active position. As homology elements, two identical copies of a rabbit β-globin intron were used which do not contain any transcription stop sites and are spliced out upon transcription. This assures that translation will start at the transgene start codon and not at any other AUG present within the homology element, which is located between the promoter and transgene in ΔAd.IR-BG. A bi-directional polyadenylation SV40pA (PA) was used to terminate transcription in the parental vector and prevent the formation of βGal antisense RNA, which could interfere with transgene expression. The control vector contained only one homology element (Ad.Co) therefore was unable to form ΔAd.IR-BG (FIG. 2III).

Transgene expression was activated in vitro upon Ad vector replication (FIGS. 3A, 3B). Rearranged genomes in cervical carcinoma cell lines were found depending on AdE1− replication (FIG. 3A). Confluent HeLa, SiHa, and Caski cells were infected with Ad.IR-BG or Ad.Co at multiplicity of infections (MOIs) of 100 (HeLa, SiHa) and 300 (Caski). 3 hours after the start of infection, the DNA synthesis inhibitor hydroxyurea (HU) was added to a subset of cells. 72 hours after infection, DNA was analyzed by Southern blot using a probe specific for the β-Gal gene. The arrows indicate the viral full-length genomes (34 kb) and the recombination product (7.3 kb). β-Gal expression was activated upon vector DNA replication in vitro (FIG. 3B). Confluent cervical carcinoma cells were infected with Ad.IR-BG, Ad.Co, or Ad.BG and treated with hydroxyurea, 72 hours after infection, cells were stained with X-Gal.

Replication and transgene expression kinetics of Ad.IR-BG and Ad.BG were compared. HeLa cells were infected with Ad.IR-BG and Ad.BG at a MOI of 100 for 90 minutes. In 12 hour intervals after the start of infection, DNA was analyzed by Southern blot and β-Gal activity was evaluated luminometrically (FIG. 4).

Figure 5B:
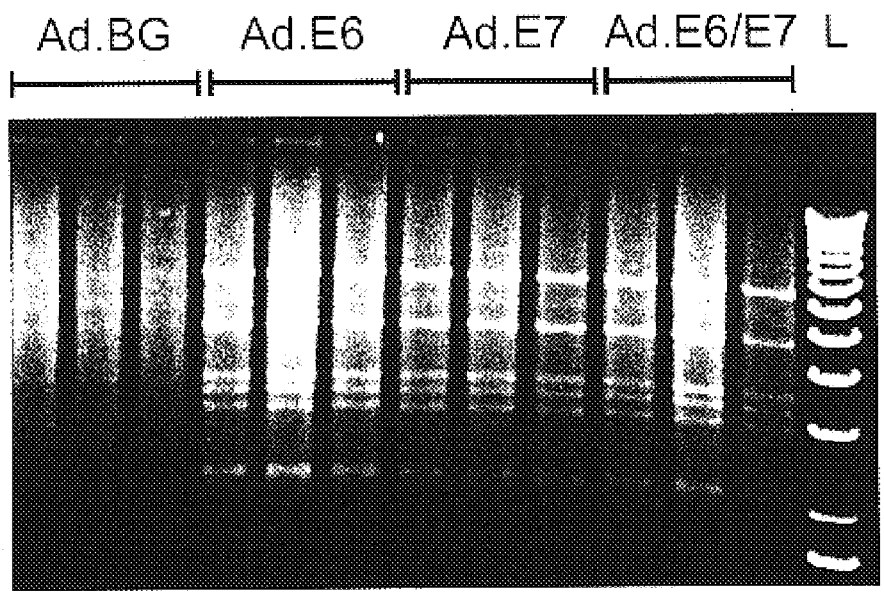
Figure 5C:
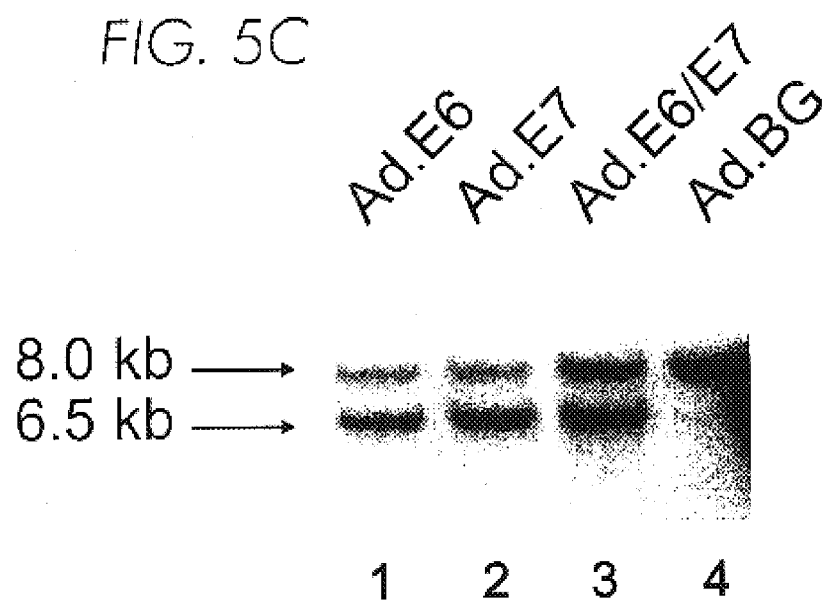

Expression of HPV E6 and E7 demonstrated AdE1− DNA replication in vitro and in vivo (FIGS. 5A, 5B, 5C). E6 and E7 expression was detected by immunoprecipitation after transfection of 293 cells with plasmids encoding the E6 or E7 genes under control of the CMV promoter. Immunoprecipitation was carried out using anti-E6 serum (FIG. 5A, lanes 1, 2, and 6) or anti-E7 serum (FIG. 5A, lanes 3, 4, and 5). The arrows indicate the E6 and E7 proteins migrating at 18 kDa and 21 kDa, respectively.

HPVE6 and HPVE7 efficiently support AdE1⁻ DNA replication in vitro (FIG. 5B). SK-HEP1 cells were infected with methylated Ad.BG, Ad.CMVE6, and Ad.CMVE7 at an MOI of 100. The gel shows the restriction pattern of cells infected with methylated Ad.BG (without E6/E7 expression), Ad.CMVE6, Ad.CMVE7, or Ad.CMVE6 plus Ad.CMVE7.

HPVE6 and HPVE7 efficiently support AdE1− DNA replication in vivo (FIG. 5C). $2 \times 10^9$ pfu of methylated Ad.BG, Ad.E6, and Ad.E7 were administered to C57BL/6 mice by tail vein infusion. Five days after infusion the Southern blot compares animals infected with methylated Ad.CMVE6 (FIG. 5C, lane 1), Ad.CMVE7 (FIG. 5C, lane 2), Ad.CMVE6 plus Ad.CMVE7 (FIG. 5C, lane 3), or Ad.BG (E1-deleted control virus) (FIG. 5C, lane 4). Vector DNA replication is only observed for HPV E6 and/or HPV E7 expressing vectors.

EXAMPLE 2

This example shows tumor specific gene expression using the replication activated Ad vector of the invention comprising two distinct parental vectors each carrying a portion of the gene of interest with an internal overlapping regions of homology. After homologous recombination, predictable genomic rearrangement results in a resolved vector that expresses the gene of interest.

Methods:

β-gal Shuttle Plasmids. To insert the RSV promoter into the adenovirus shuttle plasmid pHVad2, the RSV promoter was removed from pREP4 (Invitrogen, Carlsbad, Calif.) by Sal I and Xho I digestion and cloned into pHVad2 opened with Xho I yielding pHVad2RSV. The 5' portion of the βgal gene was cloned into this modified shuttle plasmid by releasing it from pBgalSV40 with Eco RV and Xba I double digestion and inserting it into the Eco RV and Xba I sites of pHVad2RSV forming p5'βgal.

To clone the 3' portion of the βgal gene with a polyadenylation signal into the shuttle plasmid pHVad2, pBgalSV40 was digested with Asp 718 plus Aat II, blunted, and inserted into pHVad2 opened with Eco RV creating p3'βgal.

Figure 6:
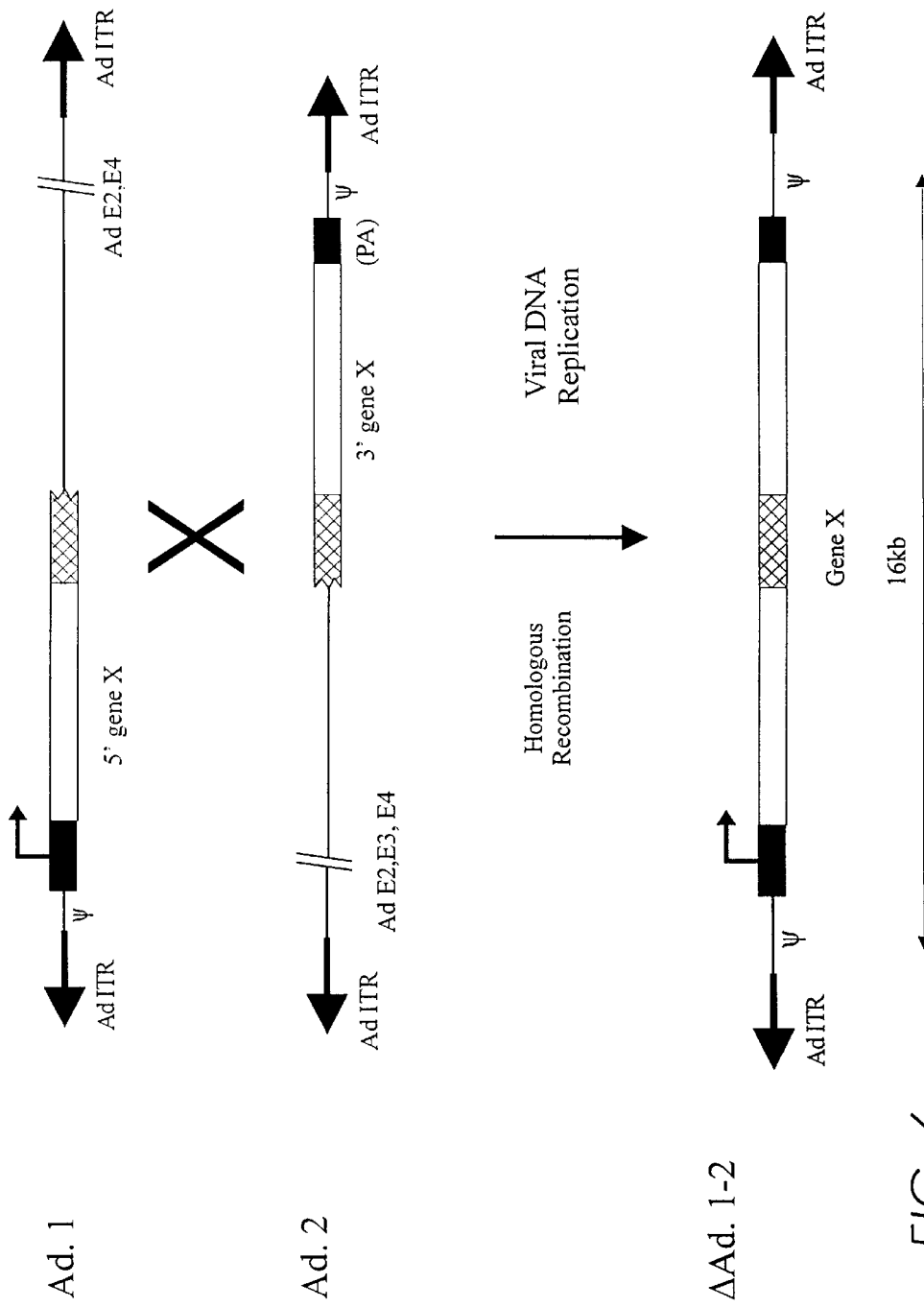
FIG. 6: A proposed mechanism of replication activated Ad vectors for tumor-specific gene expression which is dependent on recombination between two vectors, each vector containing one homology element.

Discussion:

The parental vector that carries the 5' portion of the transgene (Ad.1) contained the following elements inserted into a first generation Ad vector: A left ITR, an adenovirus packaging sequence located 3' to the left ITR, a promoter located 3' to the adenovirus packaging sequence, the 5' portion of the transgene located 3' to the promoter, genes for replication of a first generation adenovirus, and the right ITR. The parental vector with the 3' portion of the transgene (Ad.2) contained a right ITR, genes for replication of a first generation adenovirus located 3' to the right ITR, the 3' portion of the transgene located 3' to the gene for replication of a first generation adenovirus, an adenovirus packaging sequence located 3' to the transgene, and the right ITR. The transgene in AD.1 is the 5' portion of the same transgene as in Ad.2. Ad.2 has the 3' portion of the same transgene as in Ad.1. Downstream regulatory element(s) can be used depending on the goal (eg. tissue specific enhancers) and a polyadenylation signal can be employed to improved transcription. The 3' portion of the transgene must contain overlapping sequence with the 5' portion creating homologous elements for recombination and reconstitution of the complete functional gene (FIG. 6).

Co-infection of these two parental vectors (described above) in adenovirus replication permissive cells resulted in the reconstitution of a complete functional gene expression cassette mediated by homologous recombination.

Co-infection of 293 cells allowed for the creation and purification of the corresponding deleted vector containing the functional gene expression cassette flanked on both side by the packaging signal and 5' adenovirus ITR.

Genetic material undesired in the deleted vector but helpful in the first generation vectors was cloned after the 5' portion or 3' portion of the transgene in the first or second vector, respectively.

Recombination between two first-generation vectors was precise and allowed reconstituting a functional gene. As a proof of principle, two fragments of the lacZ reading frame were cloned into separate Ad vectors, such that neither could express functional βGal. Upon coinfection of the two vectors, the reading frame was restored by homologous recombination yielding functional βGal expression (FIG. 7). The recombined genome was packaged and could be purified by CsCl gradients. The restoration of the βGal open reading frame, leading to the production of an active enzyme through recombination, was strictly dependent on viral DNA replication. Therefore co-infection of the two viruses will activate gene expression specifically in tumor cells.

A generalized scheme is shown for proposed replication activated Ad vectors for tumor-specific gene expression that is dependent on the recombination between two vectors, each vector containing one homology element (FIG. 6).

Figure 7A:
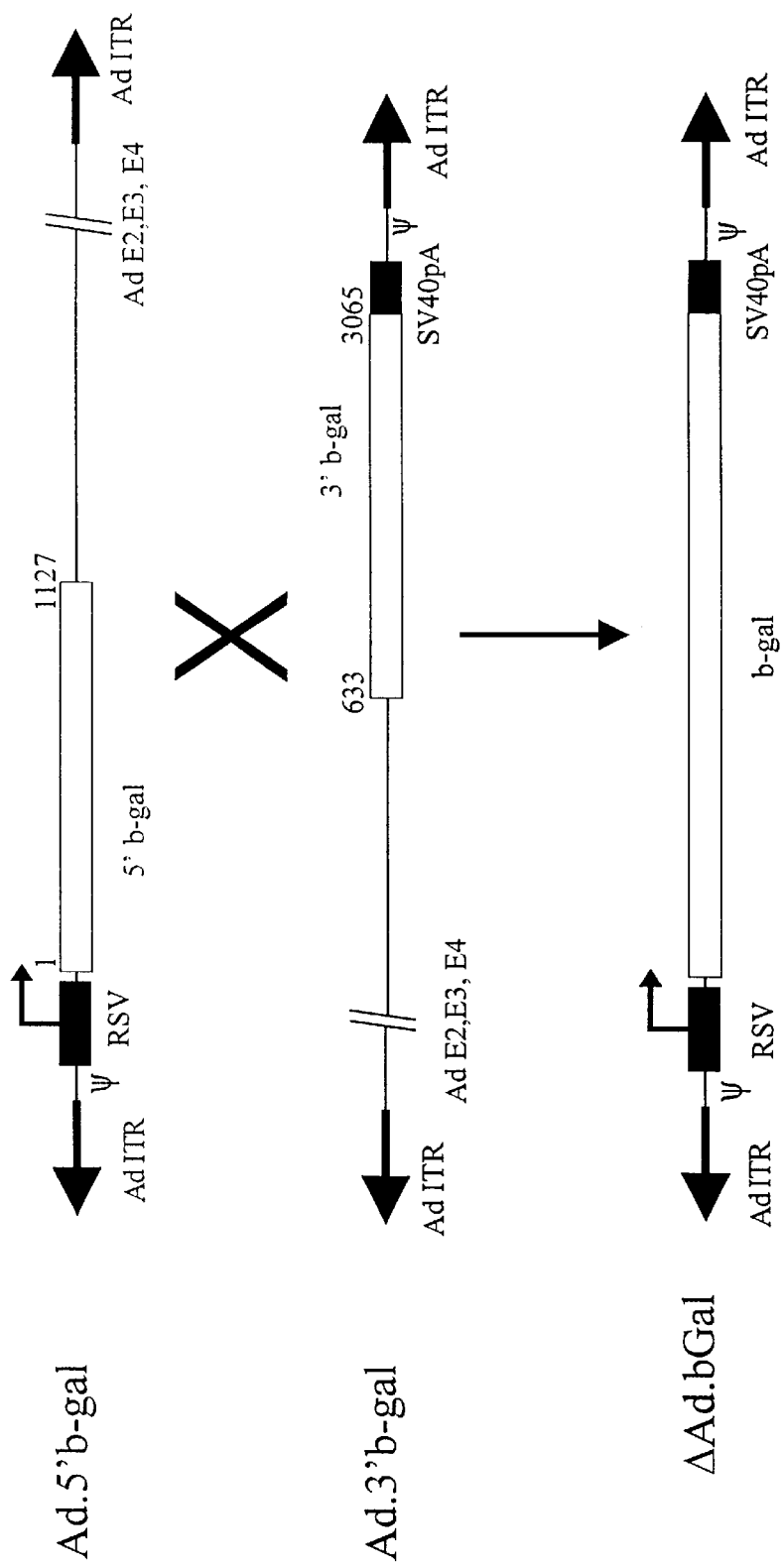
FIGS. 7A, 7B: Activation of transgene expression upon co-infection of two Ad vectors each carrying one half of the transgene.
Figure 7B:
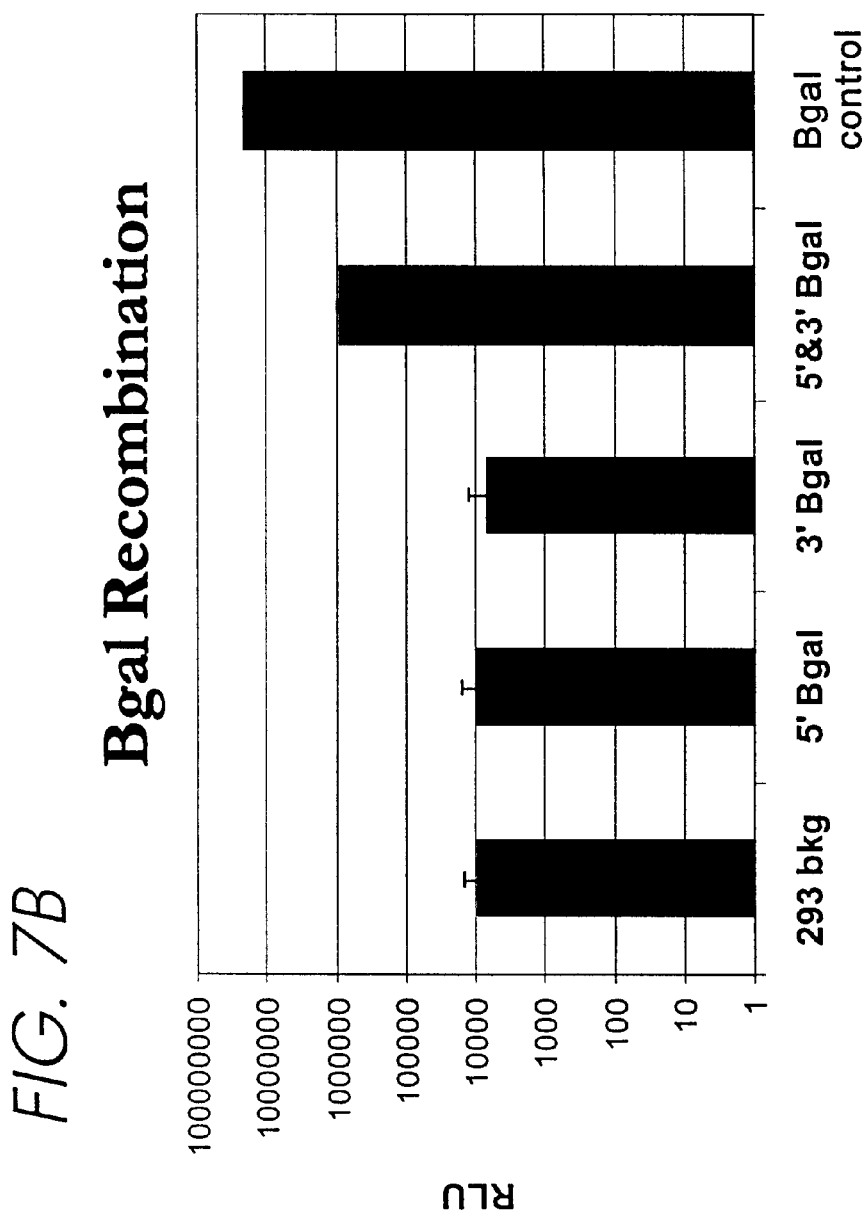

Transgene activation and expression occurs upon co-infection of two Ad vectors each carrying one half of the transgene (FIG. 7). Two fragments composing the complete β-Gal gene were individually inserted in opposite orientations into the E1 region of Ad vectors. The two β-Gal gene fragments had an overlapping homology region of ~500 bp. The complete lacZ gene was reconstituted upon co-infection of Ad5'bGal and Ad3'bGal and recombination via the region of homology (FIG. 7A). Quantification of β-galactosidase activity in 293 cells was measured after infection with Ad5'bGal, Ad3'bGal, or a combination of both vectors (FIG. 7B; RLU: relative light units).

EXAMPLE 3

This example describes a use of the one vector system described in Example 1.

Clinical applications of tumor gene therapy approaches should exhibit tumor specific delivery or expression of therapeutic genes. Another challenge is targeting every cell in the primary tumor and all metastases. We have developed a system that attempts to address these requirements. Our approach is based on first-generation E1 and/or E3 deleted Ad vectors, which have the potential to transduce all tumor sites after systemic application (Hitt, M. M., Addison, C. L., Graham, F. L. 1997 Advances in Pharmacology 40, 137–205). Notably, the vast majority of Ad vectors infused into the tail vein of mice are found in the liver (Vrancken Peeters, et al. 1996 BioTechniques 20, 278–285). Therefore, in this study we focused on targeting liver metastases. We found that the intrinsic property of cervical carcinoma cells to express HPV E6/E7 proteins supports replication of E1 deleted Ad vectors, whereas hepatocytes in vivo do not. Based on this data, we developed a new concept of replication activated transcription allowing for restricted transgene expression in hepatic metastases of a mouse tumor model.

Methods

Animals: Animal studies were performed in accordance with the institutional guidelines set forth by the University of Washington. All animals were housed in SPF facilities. Eight to 12 week old NIHS-beige-nude-xid (NIH-III) mice were purchased from Taconic (Germantown, N.Y.). These mice are deficient for B, T, and NK cells and constituted the best model for transplantation into the liver among the several tested immunodeficient strains (SCID, Nude, C.B17). Portal vein cannulation and cell infusion is described elsewhere (Vrancken Peeters, et al. 1996 BioTechniques 20, 278–285; Vrancken Peeters, M. J., et al. 1997 Hepatology 25, 884–8). Briefly, a silicon tube was inserted into the portal vein and an adhesive (Histoacryl Blau, Braun, Melsungen, Germany) was used to secure the tip. The distal end of the cannula was placed in a subcutaneous pocket. The next day, 1.5–3×106 cells singly suspended in 300 ml of Dulbecco's Modified Eagle Medium (DMEM) were infused into the portal vein over a time period of 5 min. All animals were monitored for tumor development and sacrificed before day 21 to avoid large tumors and development of ascitis according to guidelines set by Animal Care Committee at the University of Washington. For subcutaneous tumors, $1\times10^7$ cells in 100 ml DMEM were injected into the right and left inguinal region of NIH-III mice. Adenovirus injections were performed by tail vein infusions of 200 ml adenovirus diluted in DMEM. For injection into subcutaneous tumors, the viruses were diluted in 50 ml of DMEM.

Histology: Liver sections were frozen in OCT compound (Miles, Inc. Elhart, Ind.) and sectioned (10 $\mu$m). Liver sections were stained with 5-bromo-4-chloro-3-indolyl β-D-galactoside (X-Gal) and/or hematoxylin and eosin or neutral red as described earlier (Lieber, A., et al. 1996 J Virol 70, 8944–60).

A potentially important feature of this new expression system is that the transgene product accumulates late in the infection cycle. To prove this, βGal activity was measured in HeLa cells at different time points after infection with Ad.IR-BG or the reference Ad.BG virus (FIG. 4). In parallel, the kinetics of vector replication was assessed based on accumulation of ΔAd.IR-BG or Ad.BG genomes. Expectedly, the expression kinetics found for Ad.IR-BG correlated exactly with accumulating ΔAd.IR-BG genomes. Ad.BG mediated more rapid accumulation of β-galactosidase activity than Ad.IR-BG and already reached 75% of the maximal enzyme activity 48 hours post infection compared to only 47% obtained by Ad.IR-BG.

Discussion:

Transgene expression in vitro was highly specific for vector DNA replication in the cervical carcinoma cell lines SiHa and Caski and correlated with the formation of the transcription competent genome derivative ΔAd.IR-BG. HeLa cells, however, showed some background expression that was independent of ΔAd.IR-BG formation. Importantly, no unspecific expression in HeLa cell derived metastases was observed after infection with the recombination incompetent control vector, Ad.Co, in vivo suggesting that artificial culture or infection conditions in vitro induced ΔAd.IR-BG independent expression in this particular cell line. Previously, we have shown that culture conditions in vitro can induce unspecific transgene expression from regulatory elements contained in the Ad genome.

A single systemic vector administration of Ad.IR-BG achieved tumor specific βGal expression in every metastasis. No extra-tumoral transgene induction was observed. Considering that the majority of administered vector particles infect hepatocytes and only a minor fraction transduces metastatic tumor cells, this demonstrates the selectivity of transgene activation in vivo. Multiple vector infusions increased the fraction of transgene expressing tumor cells per metastasis. At this higher dose, scarce expression was observed in normal liver tissue predominantly in the vessel wall of the portal vein suggesting that the number of viral genomes reaches a threshold that is required to induce low level vector DNA replication in this tissue. However, the virus load causing significant extra-tumoral expression is significantly greater than what is needed to achieve transgene activation in all metastases.

A wide variety of cell lines derived from tumors other than cervical carcinomas can also efficiently support AdE1−DNA. Furthermore, it is thought that in tumors associated with DNA viruses (EBV, HBV, polioma virus etc.), viral gene products can functionally substitute for adenoviral E1 proteins (Gjorup, O. V., et al. 1994 Proc Natl Acad Sci U S A 91, 12125–9; Schaack, J., et al. 1996 Virology 216, 425–30; Tevethia, M. J. & Spector, D. J. 1984 Virology 137, 428–31; Tevethia, M. J. & Spector, D. J. 1989 Prog Med Virol 36, 120–90). Consequently, the presented replication activated expression system should allow for specific transgene expression in a variety of tumor types. Representatively, we demonstrated this in liver metastases derived from a colon carcinoma cell line.

Our study focused on the analysis of tumor specific transgene expression as a prerequisite for the employment of an oncolytic effector gene. Replacement of the reporter gene βGal with genes inducing apoptosis (Hanahan, D. & Weinberg, R. A. 2000 Cell 100, 57–70) or converting subsequently administered prodrugs to toxic forms (Dachs, G. U., et al. 1997 Oncol Res 9, 313–25) should mediate a highly specific anti-tumor effect. Due to the specific transgene expression kinetics, the replication activated expression system has the potential to express pro-apoptotic or cytolytic gene products at a time point when viral replication is completed, thereby facilitating the release and spread of de novo produced virus. Furthermore, enzyme/prodrug strategies in combination with our replicating Ad.IR vectors may allow for a precise timing of drug administration to facilitate virus dissemination and also mediate an advantageous bystander effect. Our strategy generates a functional promoter/gene constellation only upon viral DNA replication and thus represents a new principle of selective transcriptional activation, which can be applied to any type of conditionally replicating Ad vector.

Figure 8:
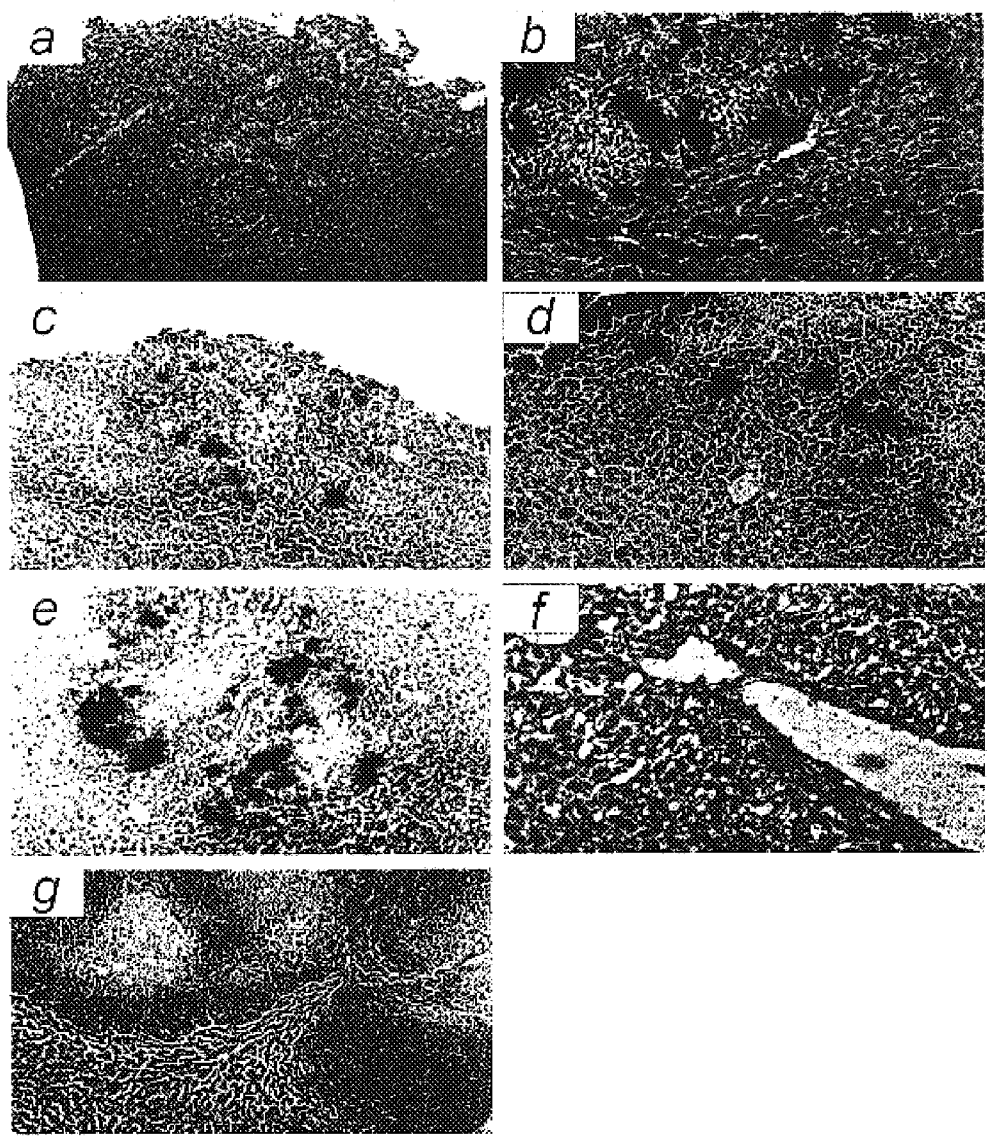
FIG. 8: Tumor specific beta-Gal expression from Ad.IR-BG in hepatic metastases derived from HeLa cells.

Tumor specific β-Gal expression from Ad.IR-BG was demonstrated in hepatic metastases derived from HeLa cells (FIG. 8). $2\times10^6$ HeLa cells were transplanted into immunodeficient NIH-III mice via a permanently placed portal vein catheter. A) Micrometastases without significant central necrosis developed in the liver after 14 days and were easily distinguished in liver sections. Liver tissue sections were stained with H & E, X-Gal and counter-stained with neutral red. B) Single tail vein injection 14 days post transplantation of the standard Ad.BG vector ($5\times10^9$) (FIG. 8B). Liver tissue sections were stained with H & E, X-Gal and counter-stained with neutral red. $5\times10^9$ pfu of Ad.IR-BG were infused at day 14 post-transplantation. Liver tissue sections were stained with (hematoxilin and eosin) H & E, X-Gal and counter-stained hematoxilin (FIGS. 8C & 8D). Injection of $5\times10^9$ pfu of Ad.IR-BG at day 14 and 15 post transplantation showed a higher fraction of tumor cells expressing βGal (FIGS. 8E & 8F). Arrows in F show single blue cells in normal liver tissue predominantly in the vessel wall of the portal vein. Liver tissue sections were stained with H & E, X-Gal and counter-stained hematoxilin. The same viral dose ($2\times5\times10^9$ pfu) of the Ad.Co vector did not result in any X-Gal staining (FIG. 8G). Liver tissue sections were stained with H & E, X-Gal and counter-stained hematoxilin.

Figure 9:
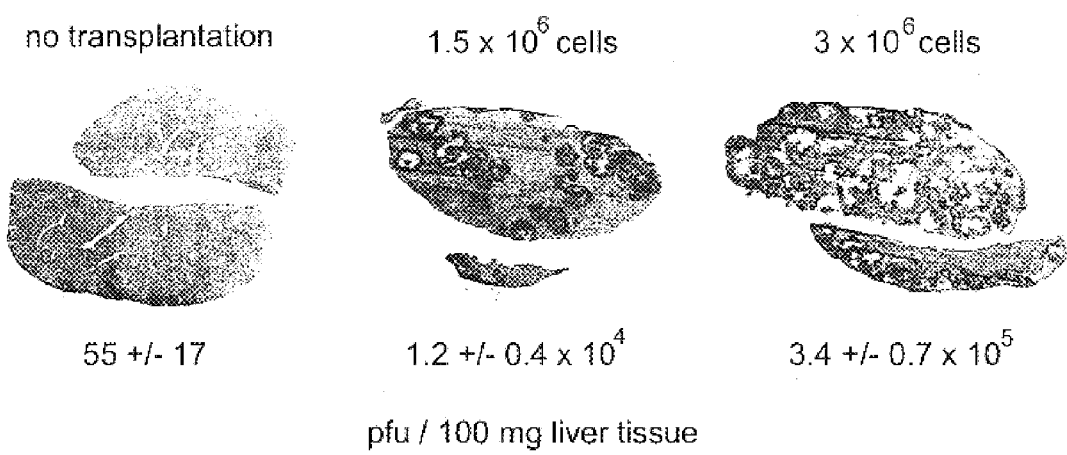
FIG. 9: Productive AdE1– replication in hepatic metastases in vivo.

Productive AdE1– replication in hepatic metastases was demonstrated in vivo (FIG. 9). $7\times10^9$ pfu Ad.IR-BG were injected into NIH-III mice without transplantation (FIG. 9, left panel), or mice that received a transplantation of $1.5\times10^6$ or $3\times10^6$ HeLa cells (FIG. 9, middle and right panel, respectively). Four days after virus infusion, part of the liver was subjected to X-Gal staining. 100 mg of liver tissue from different liver sections was homogenized, freeze/thawed, and aliquots were added to confluent 293 cells for plaque assay. The number of plaques that developed after 4 days was counted (N=4) and expressed as pfu per 100 mg tissue.

Replication dependent and tumor specific transgene expression was demonstrated in LOVO cells after infection with Ad.IR-BG (FIG. 10). The colon carcinoma cell line LOVO was infected with Ad.Co, Ad.BG, and Ad.IR-BG at MOI of 250 (FIG. 10). Normal NIH-III mice and mice bearing LOVO cell derived hepatic metastases, were infused with $5\times10^9$ pfu of Ad.IR-BG at day 14 and 15 after transplantation (FIG. 10). Day 4 after infusion tissue section were stained with X-Gal and counter-stained with hematoxilin.

EXAMPLE 4

This example describes a specific use of the two vector system of example 2.
Methods:
Rep 78 Shuttle Plasmids. Preliminarily, the rep 78 gene was cloned with a polyadenylation signal into a convenient vector. The SV40 polyadenylation signal was released from pREP4 by Xho I and Sal I double digestion and inserted into Xho I digested pBSK(+) (Stratagene, La Jolla, Calif.) yielding pBS.SV40PA. The rep 78 gene was removed from pCMVR78 by Cla I and Xho I double digestion and inserted in front of the polyadenylation signal by opening pBS.SV40PA with Cla I and Xho I forming pBS.rep78.

In order to clone the 5' portion of the rep 78 gene into a shuttle vector, the HS-4 insulator element from the chicken γ-globin locus was first removed from pSLJCa by Xho I digestion, blunted, and inserted into pHVad2 which had been opened with Bam HI and blunted yielding pHVad2.HS4. Next, the 5' portion of the Rep 78 was released from pBS.rep78 by Eco RV and Xmn I double digestion and cloned into Eco RV digested pHVad2.HS4 forming pHVHS4.5'rep. Lastly, the ApoEhAAT promoter was cloned into this shuttle plasmid by removing the promoter from pLXApoEhAAT.hFIX.bPA by Spe I and Cla I double digestion, blunting it, and inserting it into pHVHS4.5'rep opened with Eco RV yielding p5'rep78.

Figure 11A:
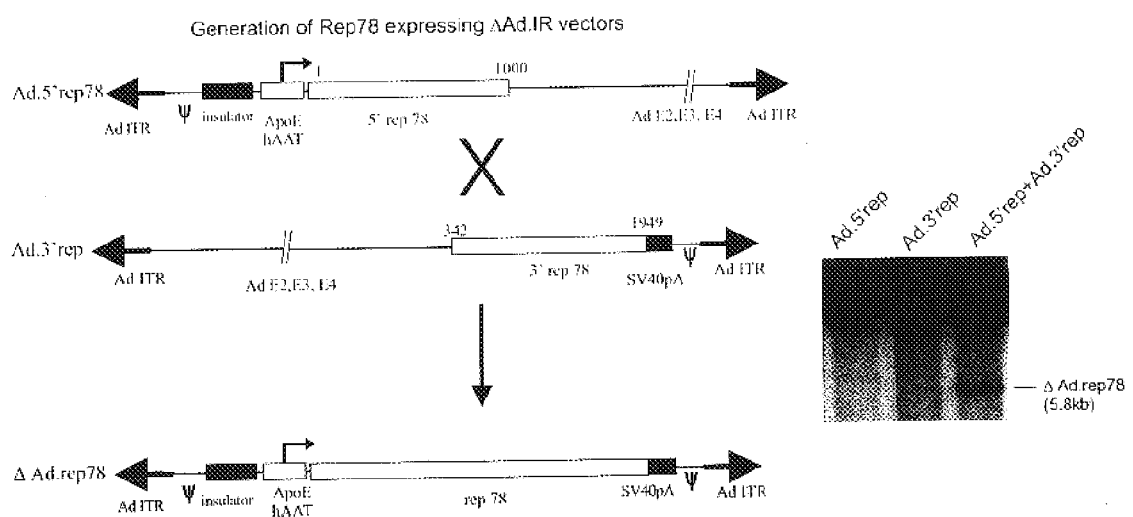
FIGS. 11A, 11B: Generation of Rep78 expressing Ad vectors by recombination between two vectors.

In order to clone the 3' portion of the rep 78 gene into a shuttle vector, the 3' portion of the rep 78 gene plus its polyadenylation signal were released from pBS.rep78 by Nco I and Asp 718 doubled digestion, blunted, and inserted into Eco RV digested pHVad2 creating p3'rep78.
Discussion:
This principle was employed to produce vectors deleted for Ad genes expressing toxic or pro-apoptotic genes. In one example, the ΔAd.IR vectors were produced and they expressed the AAV rep78, which is known to strongly inhibit Ad replication preventing the generation of rep 78-expressing vectors by standard methods. The 5' part of this modified rep78 gene was cloned into one vector while the 3' part was placed in another, each having a 658 bp long common region (FIG. 11A). Both vectors were successfully produced at normal titers. Upon co-infection into 293 cells, the expression of functional, reconstituted rep78 was demonstrated by rescue of an AAV ITR cassette from a plasmid or adenovirus backbone (FIG. 11B) with subsequent site-specific integration into ΔAVS1. Also shown was the production of ΔAd.IR vectors expressing rep78 (ΔAd.rep78). Expression of Rep 78 after infection with ΔAd.rep78 was demonstrated by Western blot. This is the first example of a rep-expressing Ad vector.

Figure 11B:
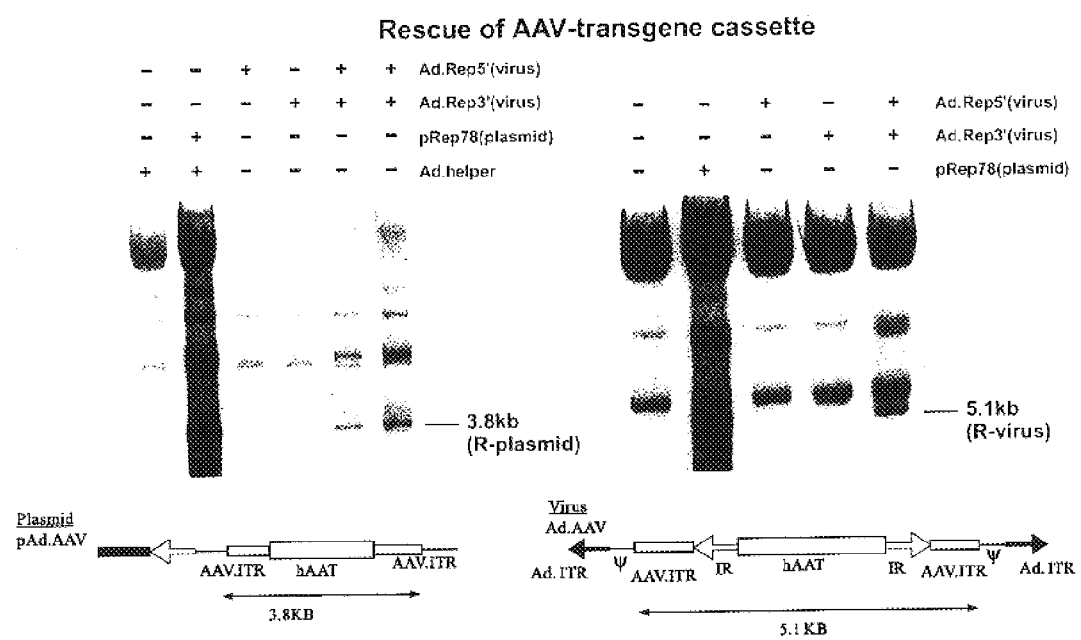

Rep78 expressing Ad vectors was generated by recombination between two vectors (FIGS. 11A, B). The same strategy outlined in FIG. 6 was employed for vectors with rep 78 as a transgene. The Ad5'rep vector also contained the ApoEhAAT promoter shielded by an HS-4 insulator. The region of homology between the two fragments of the rep78 gene was 658 nt in length. Southern blot analysis of ΔAd.rep78 genomes showed the expected 5.8 kb ΔAd.rep78 genome which was only observed upon coinfection of both Ad5'rep and Ad3' rep into 293 cells (FIG. 11A). Southern Blot analysis for rescue of the recombinant AAV genome from plasmid DNA by Rep78 expressed from pCMVrep78 and ΔAd.rep78 shows the expected rescue product of 3.8 kb (R-plasmid; FIG. 11B). Southern Blot analysis for rescue of the recombinant AAV genome from Ad.AAV viral vector genomes by Rep78 expressed from pCMVrep78 and DAd.rep78 showed the expected rescue product of 5.1 kb (R-virus; FIG. 11B)

EXAMPLE 5

This example describes the use of the two vector system of example 2 to promote vector spread throughout tumor cells.
Methods:
Ad.i-κβM. Ad.ikBM contains the 1.0 kb cDNA for the dominant negative IkBA (Di Donato, J., et al, Mol.Cell.Biol. 16: 1295–1304, 1996) fused at the 5' end to a hemagglutinin tag. The ikBM gene was inserted into Ad.PGK between the phosphoglycerokinase PGK promoter and the bPA signal (Kay, M. A. et al. Hepatology 21: 815–819, 1995). AdikBM was generated by recombination in 293 cells with pJM17 (Microbix, Toronto, Ontario, Canada). The plaque titer was determined on 293 cells. The presence of replication-competent adenovirus and contamination with endotoxin were excluded by tests described earlier (Lieber et al. J. Virology 71: 8798–8807, 1997).
Discussion:
One challenge in tumor gene therapy remains in the application of these recombinant adenoviral vectors. Efficient gene-based cancer therapy depends not only on primary gene transfer to a portion of tumor cells, but also on efficient replication and dissemination of the vectors to the surrounding tumor tissue, in order to achieve a complete killing. We hypothesized that inducing apoptosis when viral replication was completed would support release of de novo produced virus from primarily-infected cells, therefore spreading to neighboring tumor cells. We used the two vector system to induce apoptosis late in viral replication and to support viral spread throughout the tumor. In our model of hepatic metastesis with several human tumor cell lines derived from cervical, colon, breast, or lung tumors, we have been able to demonstrate that a new system of adenoviral vectors could drive transgene expression exclusively in metastesis, and targeted all metastesis, in a replication-dependent manner.

Figure 12:
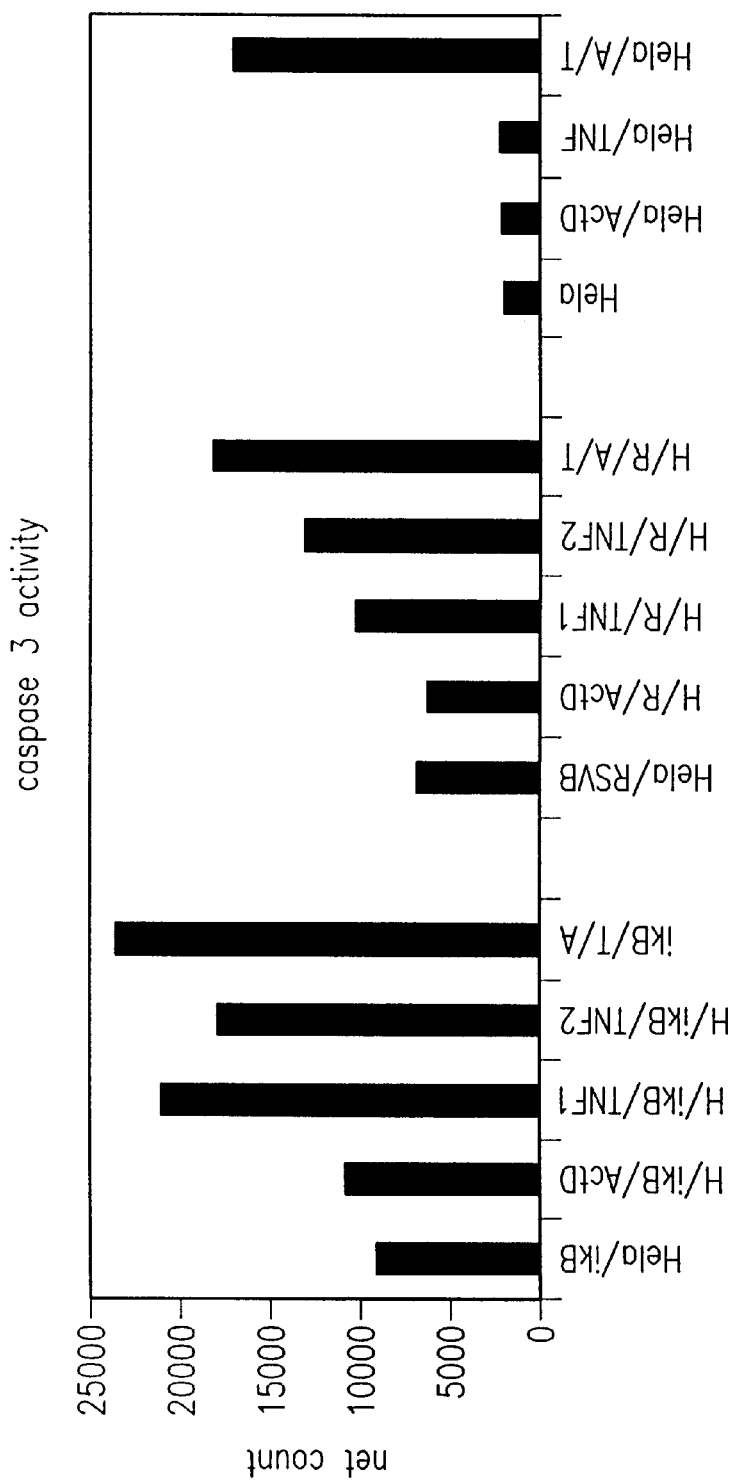
FIG. 12: A fluorescent caspase 3 activity assay.

In another example, we employed an E1-deleted adenovirus expressing a dominant negative iκB mutant (Ad.ikBM) to block NF-kB activation in selected tumor cell lines, thereby sensitizing them to apoptotic stimuli such as TNF. We observed that adenovirus-mediated ikBM expression induced apoptosis in HEK293 and HeLa cells upon TNF stimulation, as measured by cell death and caspase activity assays (FIG. 12). HEK293 and HeLa cells infected with a control adenovirus, Ad.GFP or Ad.hAAT, did not undergo apoptosis upon TNF treatment.

Figure 13:
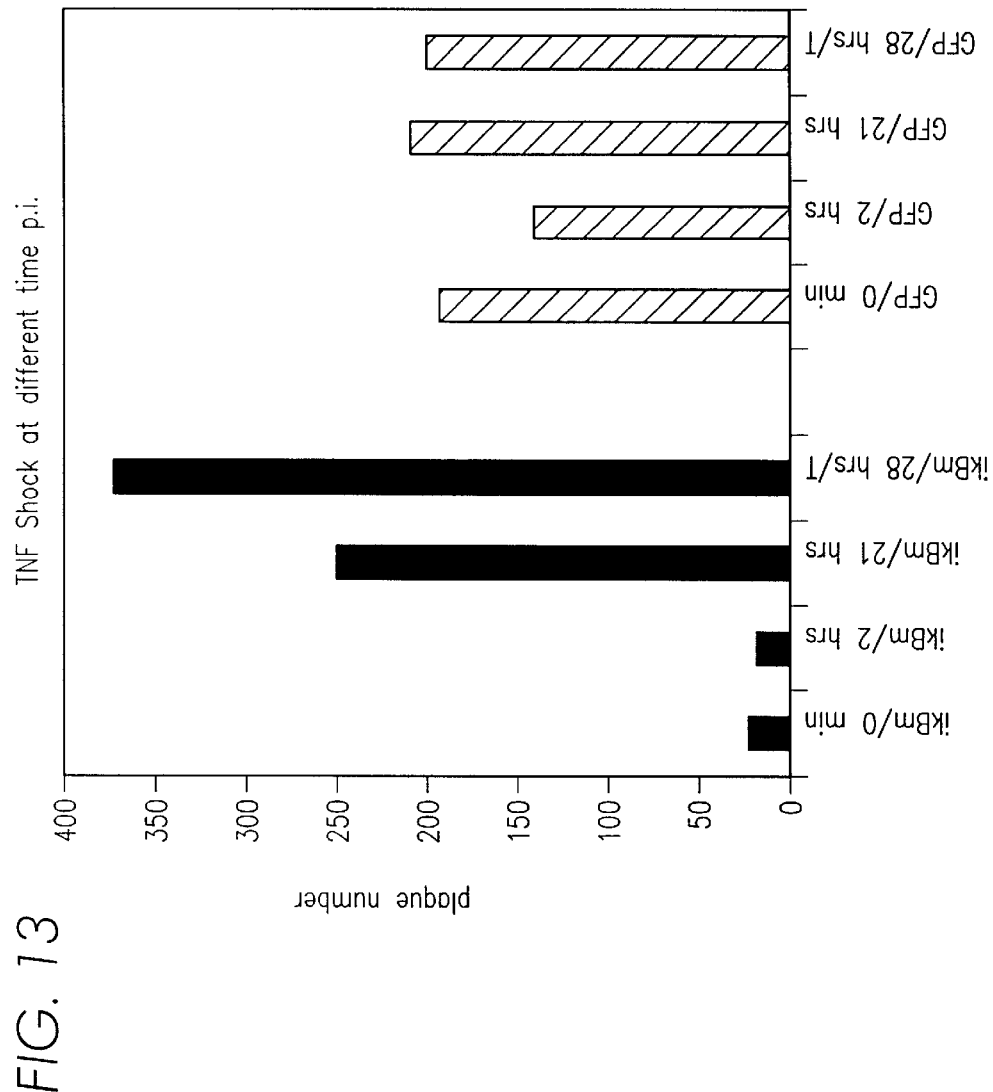
FIG. 13: TNF-induced apoptosis.

Using HEK293 cells, we found that Ad.ikBM infection plus TNF treatment after the completion of viral replication gave earlier and larger plaques than Ad.GFP or Ad.hAAT infection. This suggests that the adenovirus-mediated ikBM expression facilitated spread of the virus. We further demonstrated that TNF functions by inducing apoptosis rather than stimulating viral DNA or protein synthesis or virion assembly, by treating the Ad.ikBM-infected 293 cells with TNF at different time points during the adenovirus replication cycle (FIG. 13). TNF treatment after the completion of viral particle assembly gave more and larger plaques than treatment before or during the replication process. This result supports the conclusion that it is the TNF-induced apoptosis in ikBM-expressing cells that facilitated viral spread.

Figure 14A:
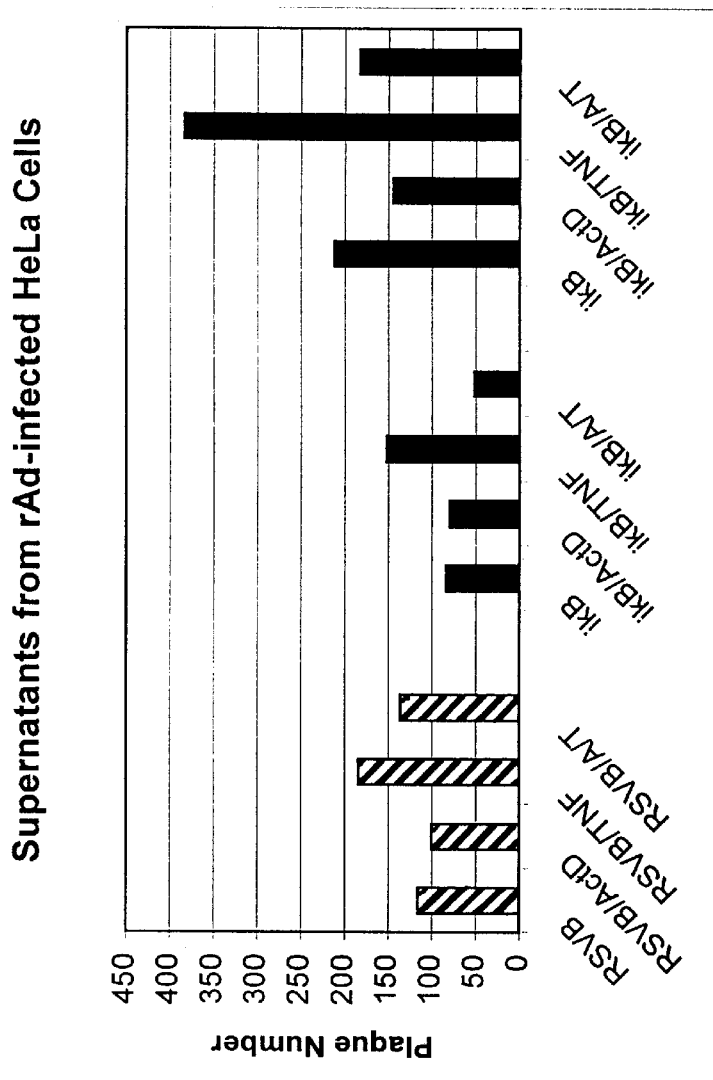
FIGS. 14A, 14B. TNF-induced apoptosis on ikBM-expressing HeLa cells facilitates the adenoviral vector release.

We also used HeLa cells as a tumor model to investigate the potential TNF-induced apoptosis and viral spread after rAd-ikBM transduction. Our experiments demonstrated that HeLa cells were subjected to TNF-induced apoptosis when sensitized by the RNA-synthesis inhibitor Actinomycin D. rAd-mediated ikBM expression had a similar sensitizing effect on HeLa cells as Actinomycin D (FIG. 14A). When we measured the released virus from the rAd-ikBM-infected HeLa cells in the culture supernatant, we found that the combination of TNFa+ikBM culture gave a higher titer than the other control cultures (FIGS. 14A and B). This proves that the induced apoptosis facilitated the release of de novo synthesized recombinant adenovirus from HeLa cells.

Figure 15:
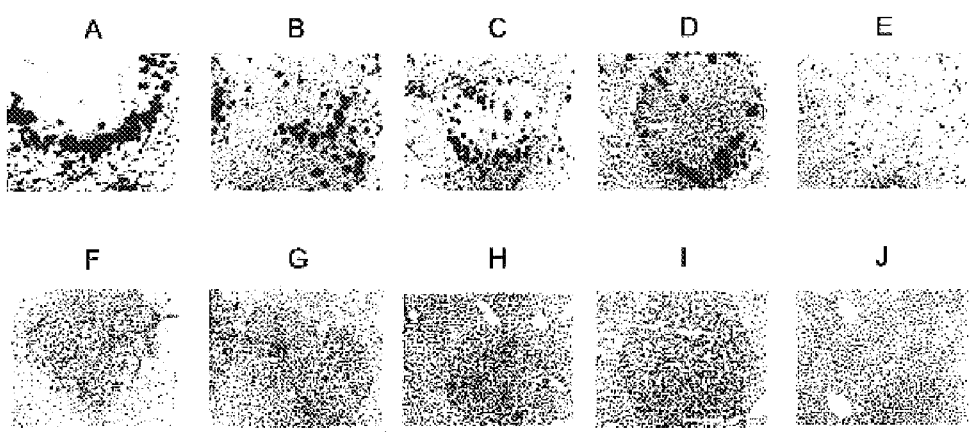
FIG. 15: Induced apoptosis facilitates recombinant Ad vector spreading in mouse model of hepatic metastasis.

In an animal model of hepatic metastesis derived from HeLa cells, our preliminary data also suggested that a larger area of transduction was achieved in tumor tissues upon rAd-mediated ikBM expression plus TNF induced apoptosis (FIG. 15). We also have preliminary data showing that ikBM expression in mouse hepatocytes in vivo is neutral or even protective against apoptotic stimuli like TNF.

The vectors described in this example can be combined with the invention of ΔAd.IR-related tumor-specific gene delivery to achieve a tumor-restricted apoptosis. The ΔAd-IR-mediated transgene expression occurs after the phases of DNA-replication and DNA sequence rearrangements. This replication-dependent system has therefore the potential to express an apoptotic or cytolytic gene when viral replication is completed, thereby to facilitate release and spread of de novo produced virus throughout the remaining tumor, in order to achieve multi-level transduction and to induce complete tumor apoptosis. A similar idea will be applied to express a suicide gene, which upon addition of a prodrug, and is often associated with a bystander effect, will kill the transduced tumor cells.

A fluorescent caspase 3 activity assay showed that rAd-ikBM-transduced HeLa cells undergo apoptosis upon TNF treatment (FIG. 12). HeLa cells infected with either the recombinant adenovirus rAd-ikBM or a control virus rAd-RSVB (R), which encodes β-galactosidase, were treated with different combinations of hTNFα (TNF or T) or/and the RNA synthesis inhibitor Actinomycin D (ActD or A). Uninfected HeLa cells were included as controls. The cell lysates were tested for the activities of one of the apoptosis-associated enzyme, caspase 3, with the specific fluorescent substrate DEVD-AMC.

TNF-induced apoptosis is demonstrated (FIG. 13). Specifically, HEK 293 cells infected with either rAd-ikBM or a control adenovirus encoding GFP were treated with hTNFα at time points of: 0 minute; 2 hours; 21 hours; or 28 hours post-infection. Plaques represent dead HEK 293 cells after different treatments. Plaques were counted and represented in a bar graph.

Figure 14B:
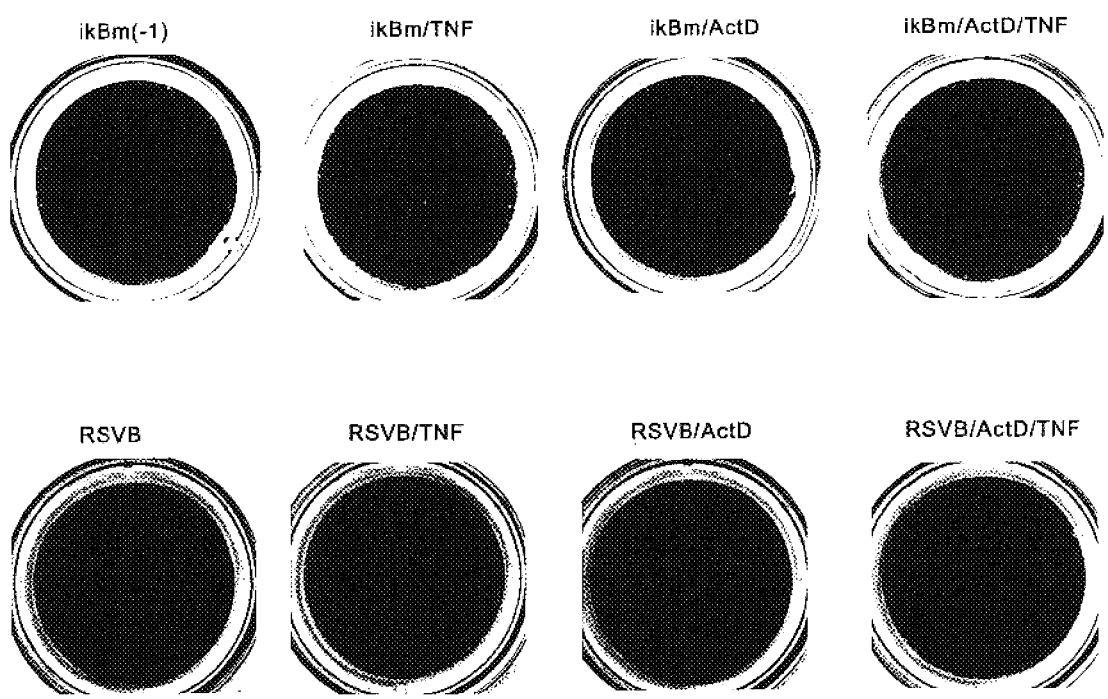

TNF-induced apoptosis of ikBM-expressing HeLa cells facilitates the adenoviral vector release (FIG. 14). HeLa cells infected with the recombinant adenovirus encoding either ikBM or β-galatosidase (RSVB) were treated with TNF (T) and/or Actinomycin D (ActD or A) (FIG. 14A). The supernatants from the different cultures were subjected to plaque assays. Plaques formed from HEK293 culture that were infected with the HeLa cell supernatants were counted either at day 3 (FIG. 14A, the left two groups) or day 5 (FIG. 14A, the most right group) and represented by the bar graph. The supernants of HeLa cell cultures with different treatments were subjected to a plaque assay (FIG. 14B). Supernatant from ikBM-transduced plus TNF treated HeLa culture induced the most plaques on the HEK 293 cells.

Induced apoptosis facilitates recombinant Ad vector spreading in mouse model of hepatic metastasis (FIG. 15). Mice modeled for hepatic metastasis with HeLa cells (except E and J are from normal mouse) were infected through tail vein with recombinant adenovirus (rAd) expressing β-galactosidase (β-gal), in a mixture with either rAd expressing the dominant negative mutant i-κ-β (ikBM) (A, B, C, F, G, E, and J) or rAd expressing the Green Fluorescent Protein (GFP) (D, H, and I). Two weeks after infection, half of the mice received repeated intravenous administration of 1 μg recombinant human TNF-alpha (A, C, F, H, E, and J), whereas the others received saline as control. All mice were sacrificed two days after TNF administration. Adjacent liver sections of 10 μm (A vs F; B vs G; C vs H; D vs I; and E vs J) were either gained with x-gal for β-gal (A–E), or immunostained by TUNNEL method for apoptotic cells (F–J).

EXAMPLE 6

This example provides supporting data that first generation Ad vectors specifically replicate in tumor cells.
Discussions:

The normal targets for adenovirus infection include quiescent, non-dividing cells, for example differentiated lung epithelial cells. The environment in quiescent cells is not suitable for viral DNA replication. In order to replicate, Ad has developed mechanisms to force the cell into the S-phase of the cell cycle. This process involves the adenoviral E1A and E1B proteins. E1A/B also mediate viral replication by transactivating viral gene expression. Consequently, viruses that are deleted for the E1A and B genes (AdE1⁻) should be disabled for viral DNA replication. AdE1⁻ viruses are widely used in gene transfer studies in vitro and in vivo and are considered replication deficient. However, a detailed study of AdE1⁻ DNA replication within transformed tumor cell lines showed the impact of replication template concentration, cell cycling, and the status of cell cycle regulators on AdE1⁻ DNA synthesis.

Ad DNA replication is only initiated upon the production of a critical threshold of early viral proteins, which in turn, is directly dependent on the number of viral genomes present in the nuclei of infected cells. The number of intranuclear viral genomes is a function of the efficiency of cellular virus internalization and nuclear import. Our data confirmed significant differences in virus internalization among the cell lines tested. Interestingly, variations in nuclear import of viral genomes were less pronounced suggesting that nuclear import of Ad genomes utilizes common cellular structures.

After equalization of infection conditions among the different cell lines, de novo viral DNA synthesis was measured by a replication assay based on selective restriction digest of replicated viral DNA. This method is more sensitive compared to Southern analysis studying the accumulation of viral DNA over time or hexon immunoflourescence staining at different times post-infection used in other replication studies. This confirms earlier observations on AdE1- viral DNA replication and demonstrates that certain factors in these cell lines can efficiently substitute for the functions of AdE1A and 1B.

Figure 16A:
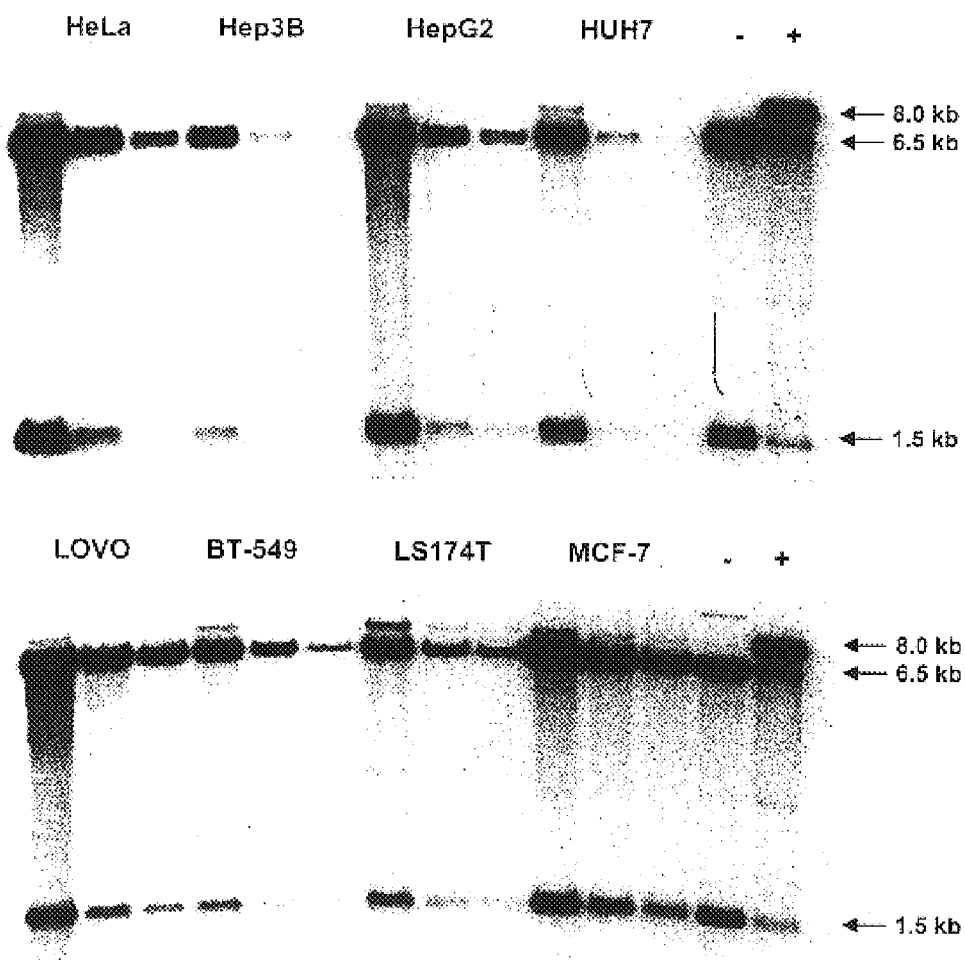
FIGS. 16A, 16B: Analysis of AdE1– DNA replication in tumor cell lines by Southern blot.

Southern blot analysis showing AdE1⁻ DNA replication in tumor cell lines (FIGS. 16A, B). Viral DNA or total DNA was analazed by Southern blot probed with a viral 8 kb HindIII fragment containing one methylation sensitive XhoI-site. Newly synthesized viral DNA is demethylated and allows for XhoI restriction, generating two fragments of 6.5 kb and 1.5 kb Ad (−). A comparison between tumor cell lines was done, cell lines were infected with 1×, 1/5, and 1/10 virus concentration, 72 h after infection, cellular DNA was extracted, digested with HindIII plus XhoI, and evaluated by Southern blot (FIG. 16A). A comparison between 293 and HeLa cells was done, Southern blot analysis of the DNA was performed 24 h after infection (FIG. 16B).

Figure 16B:
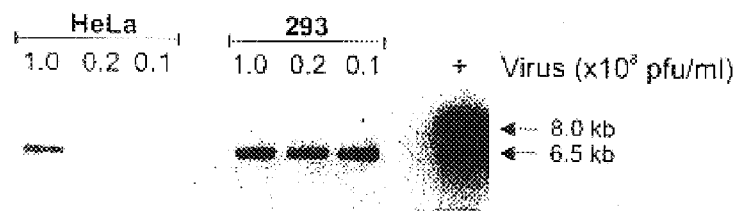

The Southern blots of FIGS. 16A and 16B were quantified by phospho-imaging and the ratio of replicated to non-replicated viral DNA was determined after correction for incomplete methylation. The data represented shown in a table (FIG. 17) is respresented as follows: 1) replication ratio at the highest virus concentration used,+=1–5, ++=6–10, +++=11–15, ++++=16–20, +++++=20–50, ++++++=>50, 2) visual cytopathic effect 72 h after start of infection at the highest virus concentration used (−=no CPE, +++=strong CPE). A table is used to show the correlation of viral DNA replication ratios with the development of CPE, p53, pRb, and p16 status of tumor cells (FIG. 17).

Figure 18:
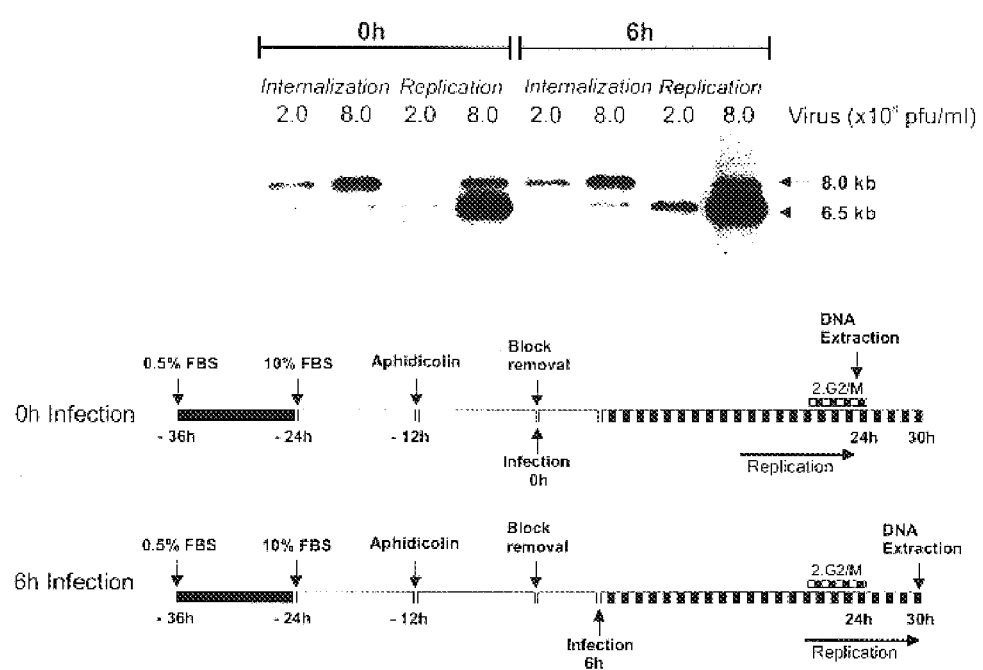
FIG. 18: AdE1– DNA replication in synchronized HeLa cells infected during different cell cycle phases.

AdE1⁻ DNA replication in synchronized HeLa cells infected during different cell cycle phases (FIG. 18). HeLa cells were cell cycle arrested. Complete cell cycle arrest was verified by FACS analysis. At 0 h and 6 h after removal of aphidicolin, HeLa cells were infected with a methylated virus. Twenty-four hours after infection, DNA samples were analyzed by Southern blot, the 6.5 kb band corresponds to demethylated (replicated) viral DNA, whereas the 8.0 kb band represents parental viral DNA.

Figure 19B:
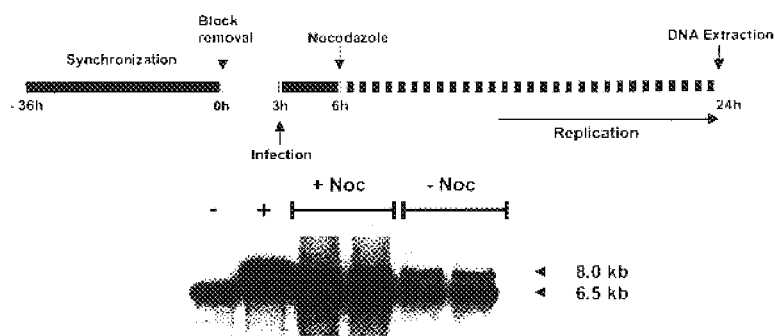

AdE1⁻ DNA replication within cells arrested in G2/M by nocodazole (FIG. 19). FACS analysis of cells 24 hours after infection (FIG. 19A). Cells were almost completely arrested in G2/M. Total cellular DNA was extracted 48 hours after infection and viral replication analyzed by Southern blot. The 6.5 kb band corresponds to demethylated (replicated) viral DNA, the 8.0 kb band represents parental viral DNA (FIG. 19B). Purified demethylated and methylated viral DNA are shown as standards (−, +, respectively).

Figure 20A:
Figure 20D:
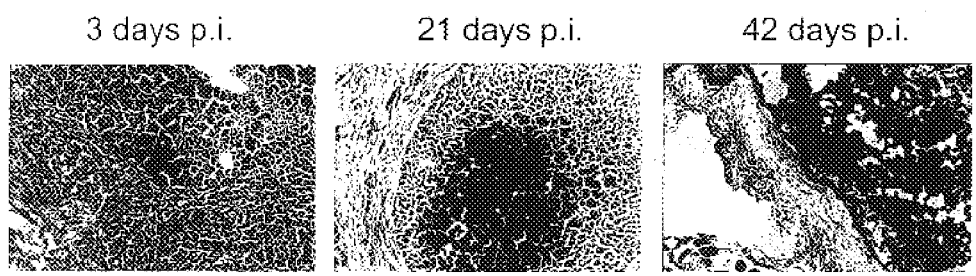

Replication of AdE1⁻ in cervical carcinoma cells (FIG. 20). AdE1⁻ DNA replication in cervical carcinoma cells. HeLa, SiHa, and Caski cells were infected at a MOI of 100 pfu/cell (HeLa, SiHa) or 300 (Caski) with a methylated, bGal expressing AdE1⁻ vector (Ad.BG) for 3 hours. 3 h after infection (uptake) and 72 hours after infection total cellular DNA was digested with HindIII and XhoI. Southern blot analysis was performed probing with a viral 8 kb HindIII fragment containing one methylation sensitive XhoI-site. Replicated viral DNA shown by a 6.5 kb fragment, parental vector DNA shown by an 8 kb fragment (FIG. 20A). A mixture methylated and unmethylated virus genomes was the standard (+). Comparison of Ad.E1⁻ DNA replication in HeLa and 293 cells was performed. Cells were infected for 90 minutes with different concentrations of methylated Ad.BG. Southern blot analysis was performed 24 h after infection (FIG. 20B). CPE mediated by AdE1⁻ infection of cervical carcinoma cell lines and 293 cells (FIG. 20C). Confluent 293, HeLa, SiHa, and Caski cells were infected at MOIs of 0.1, 1, 10, 100 (293), and 1, 10, 100, 1000 (cervical carcinoma cell lines) with Ad.BG. Twenty-four hours after infection (293 cells) or 5 days after infection (cervical carcinoma cell lines), cells were fixed and stained with crystal violet. AdE1⁻ dissemination in vivo is shown in FIG. 20D. Subcutaneous HeLa cell derived tumors were generated in NIH-III mice. Three weeks later, 3×10⁹ pfu Ad.BG (in 50 μl) were injected directly into tumors. Three, 21 or 42 days after Ad injection, tumors were excised, cryo-sectioned (10 μm), and stained.

In summary, the infectivity among the analyzed tumor cell lines varied significantly. Under equalized transduction conditions, all cell lines allowed for AdE1⁻ DNA replication regardless of their pRb, p53, and p16 status. Vector DNA replication during G2/M or after serum stimulation was enhanced.

What is claimed is:

1. A recombinant adenovirus vector comprising in order:
   a. an adenovirus left inverted terminal repeat sequence;
   b. an adenovirus packaging sequence;
   c. a heterologous promoter sequence which mediates transcription in a direction away from the adenoviral left inverted terminal repeat sequence in step a;
   d. a first inverted repeat sequence;
   e. a foreign DNA sequence to be transcribed and which is in an antisense orientation relative to the promoter sequence of step c;
   f. a second inverted repeat sequence;
   g. a gene or genes that mediates replication of the adenovirus in a transduced cell; and
   h. an adenovirus right inverted terminal repeat sequence.

2. The recombinant adenovirus vector of claim 1 further comprising a transcriptional stop site sequence located downstream of the first inverted repeat sequence, wherein the transcriptional stop site sequence arrests transcription of the foreign DNA sequence.

3. The recombinant adenovirus vector of claim 1, wherein the promoter sequence is tumor specific.

4. The recombinant adenovirus vector of claim 1, wherein the promoter sequence is a Rous Sarcoma Virus promoter sequence.

5. The recombinant adenovirus vector of claim 2, wherein the transcriptional stop site sequence is an SV40 bi-directional polyadenylation sequence.

6. The recombinant adenovirus vector of claim 2, wherein the transcriptional stop site sequence is a synthetic bi-directional polyadenylation stop site sequence.

7. The recombinant adenovirus vector of claim 1, wherein the first and second inverted repeat sequences are the same sequence.

8. The recombinant adenovirus vector of claim 1, wherein the first and second inverted repeat sequences encode excisable RNA sequences.

9. The recombinant adenovirus vector of claim 8, wherein the first and second inverted repeat sequences are a β-globin intron.

10. The recombinant adenovirus vector of claim 8, wherein the inverted repeat sequences are intron sequences with splice acceptor and splice donor site.

11. The recombinant adenovirus vector of claim 1, wherein the foreign DNA sequence encodes a gene product.

12. The recombinant adenovirus vector of claim 11, wherein the gene product is a pro-apoptotic gene product or a cytolytic gene product.

13. The recombinant adenovirus vector of claim 11, wherein the gene product is a β-galactosidase gene product.

14. The recombinant adenovirus vector of claim 11, wherein the gene product is a suicide gene product.

15. The recombinant adenovirus vector of claim 11, wherein the gene product is a dominant negative i-κ-β gene product.

16. The recombinant adenovirus vector of claim 11, wherein the gene product is a caspase gene product.

17. The recombinant adenovirus vector of claim 16, wherein the caspase gene product is a caspase-3 gene product or a caspase-6 gene product.

18. The recombinant adenovirus vector of claim 11, wherein the gene product is a radioisotope concentrator protein.

19. The recombinant adenovirus vector of claim 11, wherein the gene product is a fusion protein containing a toxic moiety and a HSV VP22 protein.

20. The recombinant adenovirus vector of claim 11, wherein the gene product is a human β-glucuronidase.

21. The recombinant adenovirus vector of claim 1, wherein the genes that mediate replication of the adenovirus in the transduced cell are E1, E2, and E4.

22. The recombinant adenovirus vector of claim 1, wherein the genes that mediate replication of the adenovirus in the transduced cell are E2, E3, and E4.

23. The recombinant adenovirus vector of claim 1, wherein the genes that mediate replication of the adenovirus in the transduced cell are E2 and E4.

24. The recombinant adenovirus vector of claim 1, further comprising an insulator DNA element.

25. The recombinant adenovirus vector of claim 24, wherein the insulator DNA element is a chicken Y-globin insulator DNA element.

26. The recombinant adenovirus vector of claim 24, wherein the insulator DNA element is a *Drosophila melanogaster* gypsy insulator DNA element.

* * * * *

SEQUENCE LISTING

<160> NUMBER OF SEQ ID NOS: 2

<210> SEQ ID NO 1
<211> LENGTH: 39
<212> TYPE: DNA
<213> ORGANISM: Artificial Sequence
<220> FEATURE:

-continued

```
<223> OTHER INFORMATION: Description of Artificial Sequence:3' PCR
      Primer

<400> SEQUENCE: 1
aaggatccgc cagccatgga ggagtttgtg ttagattat                             39

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:5' PCR
      Primer

<400> SEQUENCE: 2
agatctctaa ctaacgggac tgtagacaaa catgccac                              38
```